(12) United States Patent
Reisfeld et al.

(10) Patent No.: US 8,241,637 B2
(45) Date of Patent: Aug. 14, 2012

(54) DNA COMPOSITION ENCODING AN IMMUNOGENIC VEGF RECEPTOR PEPTIDE AND METHODS OF USE THEREOF

(75) Inventors: Ralph A. Reisfeld, LaJolla, CA (US); Andreas G. Niethammer, Heidelberg (DE); Rong Xiang, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 13/280,855

(22) Filed: Oct. 25, 2011

(65) Prior Publication Data
US 2012/0039931 A1 Feb. 16, 2012

Related U.S. Application Data

(60) Division of application No. 11/507,298, filed on Aug. 21, 2006, now Pat. No. 8,048,428, which is a continuation-in-part of application No. 10/090,183, filed on Mar. 2, 2002, now Pat. No. 7,094,410.

(51) Int. Cl.
*A61K 39/02* (2006.01)
*A61K 39/00* (2006.01)

(52) U.S. Cl. ............... 424/200.1; 424/234.1; 424/185.1
(58) Field of Classification Search .................. None
See application file for complete search history.

(56) References Cited

U.S. PATENT DOCUMENTS

2002/0032165 A1* 3/2002 Johnson et al. ................. 514/44
* cited by examiner

*Primary Examiner* — Michael Burkhart
(74) *Attorney, Agent, or Firm* — Olson & Cepuritis, Ltd.

(57) ABSTRACT

A method of inhibiting endothelial cell proliferation in a mammal is provided. The method comprises the step of administering to the mammal an effective immunological response eliciting amount of a DNA composition comprising a DNA construct operably encoding a VEGF receptor polypeptide and a pharmaceutically acceptable carrier therefor, whereby said mammal exhibits an immune response elicited by vaccine and specific to proliferating endothelial cells. The methods of this invention inhibit vascular endothelial cell proliferation in the tumor micro-environment. Angiogenesis inhibition and subsequent decrease in tumor growth and dissemination is achieved.

24 Claims, 20 Drawing Sheets

FIGURE 1

Human KDR, DNA, codons 1 – 4071

SEQ. ID NO.: 1.

```
atggagagca agtgtgtgt ggcgtgcc ctgtggctct ggctggagac ccggccgcc      60
tctgtggtt tgctagtgt ttctcttgat ctgccaggc tcagcataca aaagaccta     120
cttacaatta aggctaataa aactcttcaa attacttgca gggacagag ggacttggac    180
tggcttggc ccaataatca gagtggcagt gagcaaggg tgaggtgac tgagtgcagc     240
gatggcctct tctgtaagac actacaatt ccaaagtga tcggaaatga cactggagc     300
tacaagtgct tctaccggga aactgacttg gctcaggtca tttatgtcta tgttcaagat  360
tacagstcc cattcattgc ttctgtagt gaccacatg gagtcgtgta cattactgag    420
aacaaaaaca aaactgtggt gattccatgt ctgggtcca tttcaaatct caacgtgtca   480
ctttgtgcaa gatacccaga aaagagattt gttcctgatg gtaacagaat ttcctggac    540
agcaaggaag gcttttactat tccagctac atggatcagct atgctggcat ggtcttctgt  600
gaagcaaaa ttaatgatga aagttaccag tctattatgt acatagttgt cgtgtaggg     660
tataggattt atgatgtgt tctgagtcg tgtcatggaa ttgaactatc tgttggagaa     720
aagcttgtct taatttgtac agcaagact gactaaatg tgggattga cttcactgg      780
gaatccctt ctcgaagca tcagcctaag aaacttgtaa acgagatct aaaacccag       840
tctggagttg agatgaagaa atttttgagc accttaacta tagatgtgt aaccggagt    900
gaccaaggat tgtacacctg tgcagcatcc agtgggctga tgaccaagaa gaacagcaca     960
tttgtcaggg tccatgaaaa aacctttgtt gcttttggaa gtggcatgga atctcgtg    1020
gaagccacgg tggggagg tgtcagaatc cctgcgaagt acttggta cccacccca    1080
gaatataaat ggtataaaa tgaatacccc ttgagtcca atcaacaat taagcgggg     1140
catgtactga cgattatgga agtgagtgaa agagacagg gaaattacac tgtcatcct    1200
accaatcca ttcaaagga gaagagag catgtgctc ctctgttgt gtatgtcca        1260
cccagattg gtgagaatc tctaatctct cctgtggatt cctaccagta aggaccact    1320
caaacgctga catgtacgt ctatgccatt ctccccga atcacatca ctggtattg      1380
cagttgagg aaagagtcgc caacgagcc agcaagtg tctcagtgac aaacccatc      1440
ccttgtgaag aatggagaag tgtgaggac ttcaggagg gaaataaaat tgaagttaat   1500
aaaaatcaat ttgctctatt tgaggaaaa aacaaaactg taagtaccct tgttatccaa   1560
gggcaaatg tgtcagcttt gtacaatgt gaagcggtca acaagttcgg gagggagag    1620
aggtgatct ccttccactg taccaggggt ctgaattta cttgcaacc tgacatgcag   1680
cccactgagc aggagagagt gtctttgtgg tgcactcag acagatctac gttcgagaac   1740
ctcaaatggt acaagcttgg cccacagcct atgccaatca atgtgggaga gttgccaca   1800
cctgtttgca agacttggga tacttttgg aagttgaatg ccaccatgtt ctctaatagc    1860
acaaatgaca ttttgatcat ggagttaaag aatgcatcct tgcaggacca aggagactat  1920
gtctgccttg ctcaagacag gaagaccaag aaaagacatt gctgtgtcag gcagctcaca   1980
gtcctagagc gtgtggacca acgatcaca ggaaactgg agaatcagac gacaagtatt   2040
ggggaagca tcgagtctc atgacggca tcctggaato ccctccaca gatcatgtg      2100
tttaaagata atgagaccct tgtagaagac tcaggcattg tattgaagga tgggaacgg   2160
```

FIGURE 1 - continued

```
aacctcacta tccgcaagagt gaggaaggag gacgaaggcc tctacacctg ccaggcatgc    2220
agtgttcttg gctgtgcaaa agtggaggca ttttcataa tagaaggtgc ccaggaaaag      2280
acgaacttgg aaatcattat tctagtaggc acggcggtga ttgccatgtt cctctggcta     2340
cttcttgtca tcatcctacg gaccgttaag cgggcaatg gagggaact gaagacaggc       2400
tacttgtcca tcgtcatgga tccagatgaa ctccattgg atgaacattg tgaacgactg     2460
cctatgatg ccagcaaatg ggaattcccc agagaccggc tgaagctagg taagcctctt    2520
ggcctggtg cctttggcca agtgattgaa gcagatgcct ttggaattga caagacagca      2580
acttgcagga cagtagcagt caaaatgttg aaagaaggag caacacacag tgagcatcga    2640
gctctcatgt ctgaactcaa gatcctcatt catattgtc accatctcaa tgtggtcaac    2700
cttctagtg cctgtaccaa gccaggaggg ccactcatgg tgattgtgga attctgcaaa    2760
tttggaaacc tgtccactta cctgaggagc aagagaaatg aatttgtccc ctacaagacc    2820
aaagggcac gattccgtca agggaaagac tacgttgag caatccctgt ggatctgaaa    2880
cggcgcttgg acaggatcac cagtagccag agctcagcca gtctctgatt tgtggaggag    2940
aagtcctca gtgatgtaga agaagaggaa gctcctgaag atctgtataa ggaacttctg    3000
aacttggagc atctcatctg ttacagcttc caagtggcta aggggatgga gttcttggca    3060
tccgcaaagt gtatccaagg ggacctggcg gcaagaaata tcctcttatc ggagaagaac    3120
gtggttaaaa tctgtgactt tggcttggcc cgggatattt ataagatcc agattatgtc    3180
agaaaaggag atgctgcct ccctttgaaa tggatggcc cagaaacaat tttgacaga      3240
gtgtacacaa tccagagtga cgtctgtct ttggtgtt tgctgtgga aatattttcc       3300
ttaggtgctt ctccatatcc tgggtaaag attgatgaag aatttgtag cgatttgaaa    3360
gaagaactaa gaatgacggc ccctgattat actacaccag aaatgtacca gaccatctg    3420
gactgctggc acgggagcc cagtcagaga cccacgttt cagatttggt ggaacatttg    3480
ggaaatctct tgcaagctaa tgctcaggcag gatggcaaag actacattgt tcttccgata    3540
tcagagactt tgagcatgga agaggattct ggactctctc tgcctaactc acctgtttcc    3600
tgtatggagg aggaagaagt atgtgacccc aaatttcatt atgacaacac agcagaatc    3660
agtcagtatc tgcagaacag taagcgaaag agcggcctg tgagtgtaaa aacatttgaa    3720
gatatccgt tagaagaacc agaagtaaa gtaatcccag atgacacca gaggacagt    3780
ggtatggttc ttgcctcaga agagctgaaa acttttgaag acagaaccaa attatatcaa    3840
tcttttggtg aatggtgcc cagaaaagc agggagtctg tggcatctga aggctcaaac    3900
cagacaagcg gctaccagtc cggatatcac tccgatgaca cagaaccac cgtgtactcc    3960
agtgaggaag cagaactttt aagctgata gagattggag tgcaaaccgg tagcacagcc    4020
cagattctcc agcctgactc gggaccaca ctgagctctc ctcctgttta a              4071
```

FIGURE 2

Human KDR, protein
SEQ. ID NO.: 2

MQSKVLLAVALWLCVETRAASVGLPSVSLDLPRLSIQKDILTIKA
NTTLQITCRGQRDLWLWPNNQSGSEQRVEVTECSDGLFCKTLTIPKVIGNDTGAYKCF
YRETDLASVIYVYVQDYRSPFIASVSDQHGVVYITENKNKTVVIPCLGSISNLNVSLCA
RYPEKRFVPDGNRISWDSKKGFTIPSYMISYAGMVFCEAKINDESYQSIMYIVVVGYR
IYDVVLSPSHGIELSVGEKLVLNCTARTELNVGIDFNWEYPSSKHQHKKLVNRDLKTQS
GSEMKKFLSTLTIDGVTRSDQGLYTCAASSGLMTKKNSTFVRVHEKPFVAFGSGMESLV
EATVGERVRIPAKYLGYPPPEIKWYKNGIPLESNHTIKAGHVLTIMEVSERDTGNYTVI
LTNPISKEKQSHVVSLVVYVPPQIGEKSLISPVDSYQYGTTQTLTCTVYAIPPPHHIHW
YWQLEEECANEPSQAVSVTNPYPCEEWRSVEDFQGGNKIEVNKNQFALIEGKNKTVSTL
VIQAANVSALYKCEAVNKVGRGERVISFHVTRGPEITLQPDMQPTEQESVSLWCTADRS
TFENLTWYKLGPQPLPIHVGELPTPVCKNLDTLWKLNATMFSNSTNDILIMELKNASLQ
DQGDYVCLAQDRKTKKRHCVVRQLTVLERVAPTITGNLENQTTSIGESIEVSCTASGNP
PPQIMWFKDNETLVEDSGIVLKDGNRNLTIRRVRKEDEGLYTCQACSVLGCAKVEAFFI
IEGAQEKTNLEIIILVGTAVIAMFFWLLLVIILRTVKRANGGELKTGYLSIVMDPDELP
LDEHCERLPYDASKWEFPRDRLKLGKPLGRGAFGQVIEADAFGIDKTATCRTVAVKMLK
EGATHSEHRALMSELKILIHIGHHLNVVNLLGACTKPGGPLMVIVEFCKFGNLSTYLRS
KRNEFVPYKTKGARFRQGKDYVGAIPVDLKRRLDSITSSQSSASSGFVEEKSLSDVEEE
EAPEDLYKDFLTLEHLICYSFQVAKGMEFLASRKCIHRDLAARNILLSEKNVVKICDFG
LARDIYKDPDYVRKGDARLPLKWMAPETIFDRVYTIQSDVWSFGVLLWEIFSLGASPYP
GVKIDEEFCRRLKEGTRMRAPDYTTPEMYQTMLDCWHGEPSQRPTFSELVEHLGNLLQA
NAQQDGKDYIVLPISETLSMEEDSGLSLPTSPVSCMEEEEVCDPKFHYDNTAGISQYLQ
NSKRKSRPVSVKTFEDIPLEEPEVKVIPDDNQTDSGMVLASEELKTLEDRTKLSPSFGG
MVPSKSRESVASEGSNQTSGYQSGYHSDDTDTTVYSSEEAELLKLIEIGVQTESTAQIL
QPDSGTTLSSPPV

FIGURE 3

Human Flt-1, DNA, codons 1 - 4017
SEQ. ID NO.: 3

```
atggtcagct actggacac cgggtcctg ctgtgcgcg tgctcagctg tctgcttctc      60
acaggatcta gttcagttc aaaattaaaa gatcctgaac tgagtttaaa aggcacccag    120
cacatcatgc aagcaggcca gacactgcat ctccatgca gggggaagc agcccatcaa    180
tggtctttgc ctgaaatggt gagtaaggaa agcgaaggc tgagcataac tatatctgcc   240
tgtggaagaa atgccaaaca attctgcagt acttttaacct tgaacacagc tcaagcaaac   300
cacactggct tctacagctg caaatatcta gctgtaccta ctcaagaa gaaggaaaca   360
gaatctgcaa tctatatatt tattagtgat acaggtagac ctttcgtaga gatgtacagt   420
gaaatcccg aaattataca catgactgaa ggagggagc tgtcattcc ctgccgggtt   480
acgtcaccta acatcactgt tactttaaaa agtttccaca ttgacactt gatccctgat   540
ggaaaacgca taatctggga cagtagaaag ggcttcatca tatcaatgc aacgtacaaa   600
gaaatagggc ttctgacctg tgaagcaaca gtcaatggc atttgtataa gacaaactat   660
ctcacacatc gacaaaccaa tacaatcata gatgtccaa taagcacac agccagtc   720
aattactta aggccatac tcttgtcctc aattgtactg ctaccactcc cttgaacacg   780
agagttcaaa tgacctggag ttaccctgat gaaaaaata agagagctc catagggaga   840
cgaattgacc aagcattc ccatgccaac atattctaca gtgtcttac tattgacaaa   900
atgcagaaca aggcaaagg acttttatact tgtcgtgtaa gagctggacc atcattcaaa   960
tctgttaaca catcagtgca tatatatgat aagcattca tcactgtgaa acatcgaaaa  1020
cagcaggtgc ttgaaacgt agctggcaag cggttctacc ggctctctat gaagtgaag  1080
gcatttccct cgcgggagt tgtatggttt aaagatggt acctgcgac tgagaaatcc  1140
gctgctatt tgctcgtgg ctactcgtta attatcaagg acgtactga agaggatgca  1200
gggaattata catctttgct gagcctaaaa cagtcaatg tgtttaaaa cctcactgca  1260
actctaattg tcatgtgaa acccagatt tacgaaagg ccgtgtcatc gttccagac  1320
cccgtctctt accactggg cagagacaa atcctgactt gtaccgcata tggtatccct  1380
caacctacaa tcagtggtt ctggcacccc tgtaaccata tcattccga agcaaggtgt  1440
gactttgtt ccataatga agtccttt atcctggatg ctgcagca catgggaaac  1500
agaattgaga gtatcactca gcgcatggca atataagaag gaagactaa gatggctaga  1560
acctggttg tggctgactc tagaatttct ggaatctaca tttgcatagc ttccaataaa  1620
gttggactg tggaagaaa catcaagctt tatatcacag atgtgccaa tgggtttcat  1680
gttaacttgg aaaaaatgcc gacggaagga gaggacctga actgtcttg ctcagttaac  1740
aagttcttat acagagacgt tactggatt ttactgcgga cagttaataa cagaacaatg  1800
cactacagta ttagcagca aaaaatggcc atcactaagg agcactccat cactcttaat  1860
cttaccatca tgaatgttc cctgcaagat tcaggcacct atgcctgcag agcaggaat  1920
gtatacacag ggaagaat ctccaagaag aagaattaa aatcagaga tcaggaagca  1980
ccatacctcc tgcgaaacct cagtgatcac acagtggcca tcagcagttc caccactta  2040
gactgtcatg ctaatggtgt ccccgaacct caggatcttt ggtttaaaa caaccacaaa  2100
atacaacaag agcctggaat tattttagga ccaggaagca gaacgtgtt tattgaaaga  2160
```

FIGURE 3 - continued

```
gtcacagaag aggatgaagg tgtctatcac tgcaagcca ccaccagaa gggctctgtg    2220
gaaagttcag catacctcac tgttcaagga acctggaca agtctaatct ggagctgatc    2280
actctacact gcacctgtgt ggctgcgact ctcttctggc tcctattaac cctctttatc    2340
cgaaaaatga aaggtcttc ttctgaaata aagactgact acctatcaat tataatggac    2400
ccagatgaag ttccttgga tgagcagtgt gagcgctcc cttatgatgc cagcaagtgg    2460
gagttgccc gggagagact taaactgggc aaatcactg gaagagggc ttttggaaaa    2520
gtggttcagg catcagcatt tggcattaag aaatcaccta cgtgcggac tgtgctgtg    2580
aaaatgctga aagagggct cacgcrcagc gagtacaag ctctgatgac tgaagtaaaa    2640
atcttgaccc acattggca ccatctgacc gtggttaacc tgctggagc ctgaccaag    2700
caaggaggc ctctgatggt gattgttgaa tactgcaaat atggaaatct ctccaactac    2760
ctcaagagca aacgtgactt atttttctctc aacaaggatg cagcactaca catggagcct    2820
aagaaagaaa aaatgagcc aggctgaa caaggaaga aaccaagact agtatagtc    2880
accagcagc aaagtttga gagctccgga tttcaggaag ataaaagtct gagtgatgtt    2940
gaggaagagg aggatactga cggtttctac aaggagccca tcactatgga agatctgatt    3000
tcttacagtt ttcaagtggc cagaggcatg gagttcctgt cttccagaaa gtgcattcat    3060
cggaccctgc cagcgagaaa cattctttta tctgaaaca acgtggtgaa gattctgtga    3120
tttggccttg ccggggatat ttataagaac cccgattatg tgagaaagg agatactgaa    3180
ctctctctga aatgatgc tcctgaatcc atctttgaca aaatctacag caccaagagc    3240
gacgtgtggt cttacggagt attgctgtgg gaaatctct cttagtgg gtctccatac    3300
ccaggagtac aaatggatga ggacttttgc agtcgcctga ggggaagtat gaggatgaga    3360
gtcctgagt actctactcc tgaaatctat cagatcatgc tggactgtg gcacagagac    3420
ccaaaagaaa ggccaagatt tgcagacctt gtggaaaaac taggtgattc gctcaagca    3480
aatgtacaac aggatggtaa agactactca ccatcatcg ccatactgac aggaaatagt    3540
gggttacat actcaactcc tgccttctct gaggacttct tcaaggaaag tatttcagct    3600
ccgagtttta ttcaggaag ctctgatgat gtcagatatg taaatgctt caagttcatg    3660
agcctggaaa gaatcaaac ctttgaagaa cttttacga atgcaccto catgttgat    3720
gactaccagg ggacagcag cactctgttg gcctatccca tgctgaagcg cttcacctgg    3780
actgacagca aacccaagga ctcgctcaag attgacttga gagtaaccag taaaagtaag    3840
gagtcgggca tgtctgatgt cagcaggcc agtttctgcc attccagtg tggcaagtc    3900
agcgaaggca agcgcaaggtt cacctacgac cacgctgagc tggaaggaa actcggtgc    3960
tgctccccgc cccagacta aaactggtg gtcctgtact ccaccccaac catctag    4017
```

FIGURE 4

Human Flt-1, protein
SEQ. ID NO.: 4

MVSYWDTGVLLCALLSCLLLTGSSSGSKLKDPELSLKGTQHIMQA
GQTLSLQCRGEAAHKWSLPEMVSKESERLSITKSACGRNGKQFCSTLTLNTAQANHTGF
YSCKYLAVPTSKKKETESAIYIFISDTGRPFVEMYSEIPEIIHMTEGRELVIPCRVTSP
NITVTLKKFPLDTLIPDGKRIIWDSRKGFIISNATYKEIGLLTCEATVNGHLYKTNYLT
HRQTNTIIDVQISTPRPVKLLRGHTLVLNCTATTPLNTRVQMTWSYPDEKNKRASVRRR
IDQSNSHANIFYSVLTIDKMQNKDKGLYTCRVRSGPSFKSVNTSVHIYDKAFITVKHRK
QQVLETVAGKRSYRLSMKVKAFPSPEVVWLKDGLPATEKSARYLTRGYSLIIKDVTEED
AGNYTILLSIKQSNVFKNLTATLIVNVKPQIYEKAVSSFPDPALYPLGSRQILTCTAYG
IPQPTIKWFWHPCNHNHSEARCDFCSNNEESFILDADSNMGNRIESITQRMAIIEGKNK
MASTLVVADSRISGIYICIASNKVGTVGRNISFYITDVPNGFHVNLEKMPTEGEDLKLS
CTVNKFLYRDVTWILLRTVNNRTMHYSISKQKMAITKEHSITLNLTIMNVSLQDSGTYA
CRARNVYTGEEILQKKEITIRDQEAPYLLRNLSDHTVAISSSTTLDCHANGVPEPQITW
FKNNHKIQQEPGIILGPGSSTLFIERVTEEDEGVYHCKATNQKGSVESSAYLTVQGTSD
KSNLELITLTCTCVAATLFWLLLTLFIRKMKRSSSEIKTDYLSIIMDPDEVPLDEQCER
LPYDASKWEFARERLKLGKSLGRGAFGKVVQASAFGIKKSPTCRTVAVKMLKEGATASE
YKALMTELKILTHIGHHLNVVNLLGACTKQGGPLMVIVEYCKYGNLSNYLKSKRDLFFL
NKDAALHMEPKKEKMEPGLEQGKKPRLDSVTSSESFASSGFQEDKSLSDVEEEEDSDGF
YKEPITMEDLISYSFQVARGMEFLSSRKCIHRDLAARNILLSENNVVKICDFGLARDIY
KNPDYVRKGDTRLPLKWMAPESIFDKIYSTKSDVWSYGVLLWEIFSLGGSPYPGVQMDE
DFCSRLREGMRMRAPEYSTPEIYQIMLDCWHRDPKERPRFAELVEKLGDLLQANVQQDG
KDYIPINAILTGNSGFTYSTPAFSEDFFKESISAPKFNSGSSDDVRYVNAFKFMSLERI
KTFEELLPNATSMFDDYQGDSSTLLASPMLKRFTWTDSKPKASLKIDLRVTSKSKESGL
SDVSRPSFCHSSCGHVSEGKRRFTYDHAELERKIACCSPPPDYNSVVLYSTPPI

FIGURE 5

Mouse flk-1, DNA, codons 208 - 4344
SEQ. ID NO.: 5

```
ctgtgtccg cagccggata acctggctga ccgattccg cggacaccgc tgcagccgcg    60
gctggagcca gggcgcggt gccccgcgct ctcccggtc tgcgctgcg gggccatac   120
cgcctctgtg acttcttgc gggccaggga cggaaagga gtctgtgcct gagaaactgg   180
gtctgtgcc caggcgcgag gtcaggatg gagagcaagg cgctgctagc tgtcgctctg   240
tggttctgcg tggaacccg agccgcctct gtgggttga ctgcgattt tctccatcc   300
cccagctca gcacacagaa agacatactg acaatttgg caaatacaac ccttcagatt   360
acttgcaggg gacagcggga cctggactgg ctttggccca atgctcagcg tgattctgag   420
gaaagggtat tggtgactga atgcggcgt ggtgacagta tcttctgcaa aacactcacc   480
attccagggg tggttggaaa tgatactgga gctacaagt gctgtaccg ggacgtcgac   540
atagcctca ctgttatgt ctatgttcga gattacagat caccatcat cgcctctgtc   600
agtgaccagc atggatcgt gtacatcacc gagaacaaga caaaactgt ggtgatccc   660
tgccgagggt cgatttcaaa cctcaatgtg tctcttgcg ctaggtatcc agaaaagaga   720
tttgttccgg atggaaacag aatttcctgg gacagcgaga tagcttac tctcccagt   780
tacatgatca gctatgccgg catggtcttc tgtgaggcaa agatcaatga tgaaacctat   840
cagtctatca tgtacatagt tgtggttgta ggatatagga ttatgatgt gattctgagc   900
cccgcgcatg aaattgagct atctgccgga gaaaacttg tcttaaattg tacagcgaga   960
acagagctca atgtggggct tgatttcacc tggcactctc cacctcaa gtctcatcat  1020
aagaagattg tcaaccggga tgtgaaaccc tttcctggga ctgtggcgaa gatgttttg  1080
agcacccttga caatagaaag tgtgaccaag agtgaccaag ggaatacac ctgtgtagcg  1140
tccagtggac ggatgatcaa gagaaataga acatttgtcc gagtcacac aaagccttt  1200
attgctttcg gtagtgggat gaaatcttg gtggaagcca caggggcag tcaagtcga  1260
atcctgtgga gtatctcag ttaccagct cctgatatca aatgctacag aaatggaagg  1320
cccattgagt ccactacac aatgattgtt ggcgatgaac tcaccatcat ggaagtgact  1380
gaaagagatg caggaaacta cacggtcatc ctcaccaacc ccatttcat ggagaaacag  1440
agccatgg tctctctggt tgtgaatgtc accccagag tcgtgagca agcttgatc  1500
tgcctatgg attcctacca gtatggacc atgcagacat tgacatgcac agtctacgcc  1560
aaccctccc tgcaccact ccagtggtac tggcagctag aagaagctg ctcctacga  1620
ccggccaaa caagccgta tgcttgtaaa gaatggagac actggaggga ttccagggg  1680
ggaacaaga tcgaagtcac caaaaaccaa tatgcctga tgaaggaaa aacaaaact  1740
gtaagtacgc tggtcatcca agctgccaac gtgtcagcgt tgtacaatg tgaagcctc  1800
acaagcgg gacgaggaga gagggtcatc tccttccatg tgatcaggg tcctgaaat  1860
actgtgcaac ctgtgccca gccactgag caggagagtg tgtcctgtt gtgcactgca  1920
gacagaaata cgtttgagaa cctcacgtgg tacaagcttg gcacaggc aacatggtc  1980
caatggggcg aatcactcac accagttgc aagaacttgg atgtctttg gaactgaat  2040
ggaccatgt ttctaacag cacaaatgac atcttgattg tggcattca gaatgccct  2100
ctgcaggacc aaggcgacta tgttgctct gctcaagata gaaagaccaa gaaagacat  2160
```

FIGURE 5 - continued

```
tgcctggtca aacagctcat catcctagag cgcatggcac ccatgatcac cggaaatctg 2220
gagaatcaga caacaaccat tggcgagacc attgaagtga cttgcccagc atctggaaat 2280
cctaccccac acattacatg gttcaaagac aacgagaccc tggtagaaga ttcaggcatt 2340
gtactgaagg atgggaaccg gaacctgact atccgcaggg tgaggaagga ggatggaggc 2400
ctctacacct gccaggcctg caatgtcctt ggctgtgcaa gagggagac gctcttcata 2460
atagaaggtg cccaggaaaa gaccaactg gaagtcatta tcctcgtggg cactgcagtg 2520
attgccatgt tcttctggct ccttcttgtc attgtcctac ggaccgttaa gggggccaat 2580
gaagggaac tgaagacagg ctacttgtct attgtcatgg atccagatga attgcccttg 2640
gatgagcgct gtgaacgctt gcctatgat gcagcaagt gggaattccc caggaccgg 2700
ctgaaactag gaaaacctct tggcgcggt gccttcggcc aagtgattga ggcagacgct 2760
ttggaattg acaagacagc gactgcaaa acagtagccg tcaagatgtt gaagaagga 2820
gcaacaaca gcgagcatcg agccctcatg tctgaactca agatcctcat ccacattggt 2880
caccatctca atgtggtgaa cctcctagc gcctgcacca gccggaggg gcctctcatg 2940
gtgattgtgg aattctgcaa gttcggaaac ctatcaactt acttacgggg caagagaaat 3000
gaatttgttc cctataagag caaagggca cgcttccgcc aggcaagga ctacgttggg 3060
gagctctccg tggatctgaa aagacgcttg gacagcatca ccagcagcca gagctctgcc 3120
agctcaggct tgttgagga gaaatcgtc agtgatgtag aggaagaaga agcttctgaa 3180
gaactgtaca aggacttcct gaccttggag catctcatct gttacagctt ccagtggct 3240
aaggcatgg agttcttgc atcaaggaag tgtatccaca gggacctggc agcacgaaac 3300
attctcctat cggagaagaa tgtggttaag atctgtgact tggctggc cgggacatt 3360
tataaagacc cggattatgt cagaaaagga gatgcccgac tcccttgaa gtggatggcc 3420
ccggaaacca tttttgacag agtatacaca attcagagcg atgtgtggtc ttccgtgtg 3480
ttgctctggg aaatatttc cttaggtgcc tcccatacc ctgggtcaa gattgatgaa 3540
gaattttgta ggagattgaa agaaggaact agaatgcggg ctcctgacta cactacccca 3600
gaaatgtacc agaccatgct ggactgctgg catgaggacc ccaaccagag acctctgttt 3660
tcagagttgg tggagcattt gggaaacctc ctgcaagca atgcagca ggatggaaa 3720
gactatattg tcttccaat gtcagagaca ctgagcatgg aagaggattc tggactctcc 3780
ctgcctacct cactgttc ctgtatggag gaagaggaag tgtgcgaccc caaattccat 3840
tatgacaaca cagcaggaat cagtcattat ctccagaaca gtaagcgaaa gagccggcca 3900
gtgagtgtaa aaacattga agatatccca ttggaggaac cagaagtaaa agtgatccca 3960
gatgacagcc agacaacag tgggatggtc cttgcatcag aagagctgaa aactctggaa 4020
gacaggaaca attatctcc atctttggt ggaatgatgc ccagtaaaag cagggagtct 4080
gtggctcgg aaggctccaa ccagaccagt ggctaccagt ctggtatcca ctcagatgac 4140
acagcacca ccgtgtactc cagcgacgag gcaggacttt taaagatggt ggatgctgaa 4200
gttcacgctg actcaggac cacctgcgc tcacctcctg ttaaatgga agtggtccg 4260
tcccggctcc gccccaact cctgaaatc acgagagagg tgtgcttag atttcaagt 4320
gttgttctt ccaccaccccg gaagtagcca catttgattt tcattttgg aggagggacc 4380
tcagactgca aggagcttgt cctcagggca tttccagaga gatgccat gacccaagaa 4440
tgtgttgact ctactctctt ttccattcat ttaaaagtcc tatataatgt gccctgctgt 4500
```

FIGURE 5 - continued

```
ggtctcacta ccagttaaag caaaagactt tcaaacacgt ggactctgtc ctccaagaag 4560
tgccaacggc acctctgtga aactggatcg aatgggcaat gctttgtgtg ttgaggatgg 4620
gtgagatgtc ccagggccga gtctgtctac cttggaggct ttgtggagga tgcggctatg 4680
agccaagtgt taagtgtggg atgtggactg ggaggaagga aggcgcaagt cgctcggaga 4740
gcggttggag cctgcagatg cattgtgctg gctctggtgg aggtgggctt gtgcctgtc 4800
aggaaacgca aaggcggccg gcagggtttg gttttggaag gtttgcgtgc tcttcacagt 4860
cgggttacag gcgagttccc tgtggcgttt cctactccta atgagagttc cttcggact 4920
cttacgtgtc tcctggcctg gcccaaggaa ggaaatgatg cagcttgctc cttcctcatc 4980
tctcaggctg tgccttaatt cagaacacca aagagagga acgtcggcag aggctcctga 5040
cggggccgaa gaattgtgag aacagaacag aaactcaggg tttctgctgg gtggagaccc 5100
acgtggcgcc ctggtggcag gtctgagggt tctctgtcaa gtgcggtaa aggctcaggc 5160
tgtgtcttt cctctatctc cactcctgtc aggccccccaa gtcctcagta tttagcttt 5220
gtggcttcct gatgcagaa aaatcttaat tggttggttt gctctccaga taatcactag 5280
ccagatttcg aaattacttt ttagccgagg ttatgataac atctactgta tcctttagaa 5340
ttttaaccta taaaactatg tctactggtt tctgcctgtg tgcttatgtt      5390
```

FIGURE 6

Mouse Flk-1, protein
SEQ. ID NO.: 6

MESKALLAVALWFCVETRAASVGLTGDFLHPPKLSTQKDILTILA
NTTLQITCRGQRDLDWLWPNAQRDSEERVLVTECGGGDSIFCKTLTIPRVVGNDTGAYK
CSYRDVDIASTVYVYVRDYRSPFIASVSDQHGIVYITENKNKTVVIPCRGSISNLNVSL
CARYPEKRFVPDGNRISWDSEIGFTLPSYMISYAGMVFCEAKINDETYQSIMYIVVVG
YRIYDVILSPPHEIELSAGEKLVLNCTARTELNVGLDFTWHSPPSKSHHKKIVNRDVKP
FPGTVAKMFLSTLTIESVTKSDQGEYTCVASSGRMIKRNRTFVRVHTKPFIAFGSGMKS
LVEATVGSQVRIPVKYLSYPAPDIKWYRNGRPIESNYTMIVGDELTIMEVTERDAGNYT
VILTNPISMEKQSHMVSLVVNVPPQIGEKALISPMDSYQYGTMQTLTCTVYANPPLHHI
QWYWQLEEACSYRFGQTSPYACKEWRHVEDFQGGNKIEVTKNQYALIEGKNKTVSTLVI
QAANVSALYKCEAINKAGRGERVISFHVIRGPEITVQPAAQPTEQESVSLLCTADRNTF
ENLTWYKLGSQATSVBMGESLTPVCKNLDALWKLNGTMFSNSTNDILIVAFQNASLQDQ
GDYVCSAQDKKTKKRHCLVKQLIILERMAPMITGNLENQTTTIGETIEVTCPASGNPTP
HITWFKDNETLVEDSGIVLRDGNRNLTIRRVRKEDGGLYTCQACNVLGCARAETLFIIE
GAQEKTNLEVIILVGTAVIAMFFWLLLVIVLRTVKRANEGELKTGYLSIVMDPDELPLD
ERCERLPYDASKWEFPRDRLKLGKPLGRGAFGQVIEADAFGIDKTATCKTVAVKMLKEG
ATHSEHRALMSELKILIHIGHHLNVVNLLGACTKPGGPLMVIVEFCKFGNLSTYLRGKR
NEFVPYKSKGARFRQGKDYVGELSVDLKRRLDSITSSQSSASSGFVEEKSLSDVEEEEA
SEELYKDFLTLEHLICYSFQVAKGMEFLASRKCIHRDLAARNILLSEKNVVKICDFGLA
RDIYKDPDYVRKGDARLPLKWMAFETIFDRVYTIQSDVWSFGVLLWEIFSLGASPYPGV
KIDEEFCRRLKEGTRMRAPDYTTPEMYQTMLDCWHEDPNQRPSFSELVEHLGNLIQANA
QQDGKDYIVLPMSETLSMEEDSGLSLPTSPVSCMEEEEVCDPKFHYDNTAGISHYLQNS
KRKSRPVSVKTFEDIPLEEPEVKVIPDDSQTDSGMVLASEELKTLEDRNKLSPSFGGMV
PSKSRESVASEGSNQTSGYQSGYHSDDTDTTVYSSDEAGLLKMVDAAVHADSGTTLASP
FV

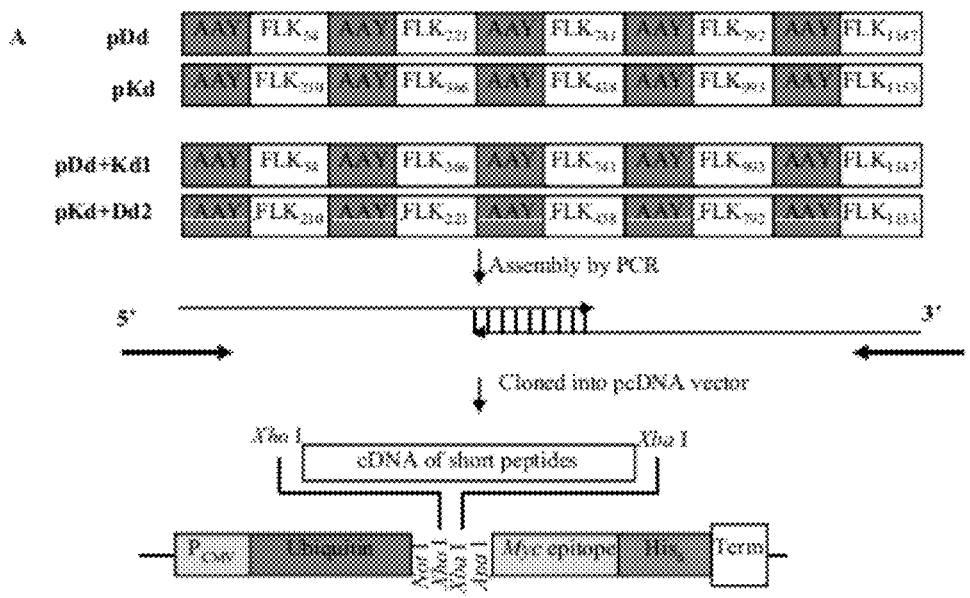
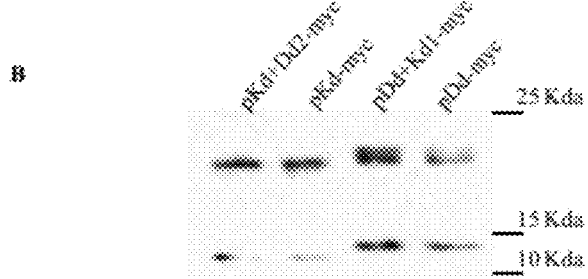
FIGURE 12

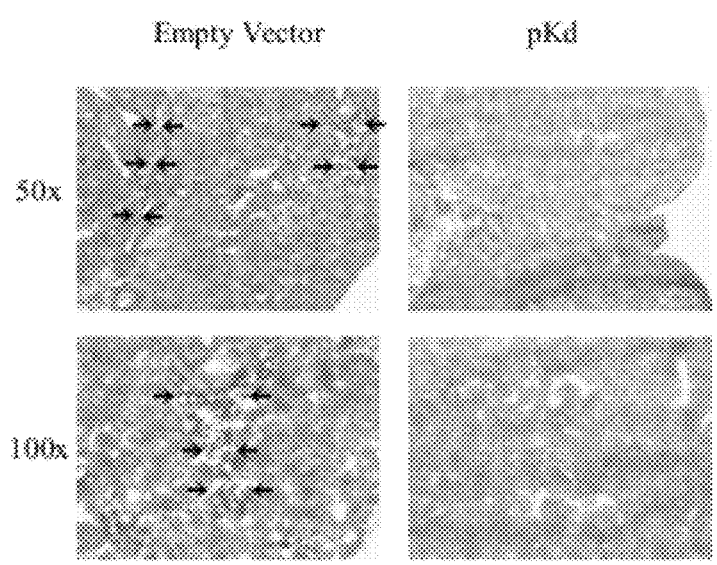
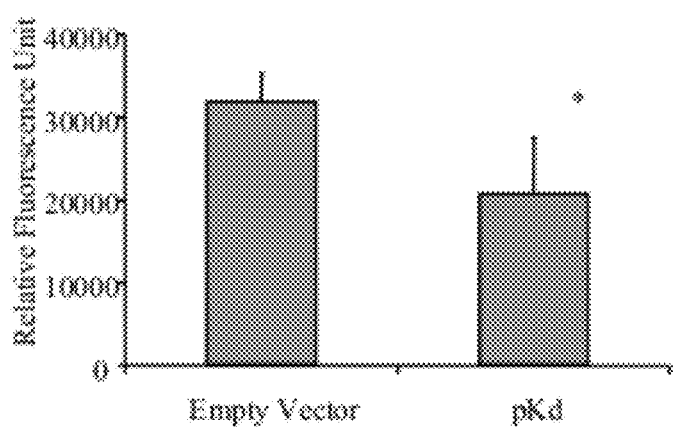
Figure 16

US 8,241,637 B2

DNA COMPOSITION ENCODING AN IMMUNOGENIC VEGF RECEPTOR PEPTIDE AND METHODS OF USE THEREOF

CROSS-REFERENCE TO RELATED APPLICATIONS

This application is a divisional of U.S. Application Ser. No. 11/507,298, filed on Aug. 21, 2006, now U.S. Pat. No. 8,048,428, which is a continuation-in-part of U.S. application Ser. No. 10/090,183, filed on Mar. 2, 2002, now U.S. Pat. No. 7,094,410, each of which is incorporated herein by reference in its entirety.

GOVERNMENTAL RIGHTS

A portion of the work described herein was supported by grant numbers 5-70373-COLON, CA83856, and CA 11571-A1 from the National Institutes of Health, as well as grant numbers DAMD17-02-01-0137 and DAMD17-02-01-0562 from the Department of Defense. The United States Government has certain rights in this invention.

FIELD OF THE INVENTION

This invention relates to deoxyribonucleic acid (DNA) compositions encoding peptides effective for eliciting an immune response against proliferating endothelial cells. More particularly this invention relates to DNA compositions encoding for an immunogenic vascular endothelial growth factor (VEGF) receptor or an immunogenic fragment thereof. This invention also relates to methods of using the DNA composition to inhibit vascular endothelial cell proliferation, tumor growth, and angiogenesis.

BACKGROUND OF THE INVENTION

Vaccines have been utilized to provide a long term protection against a number of disease conditions by very limited administration of a prophylactic agent that stimulates an organism's immune system to destroy disease pathogens before they can proliferate and cause a pathological effect. Various approaches to vaccines and vaccinations are described in Bernard R. Glick and Jack J. Pasternak, *Molecular Biotechnology, Principles and Applications of Recombinant DNA*, Second Edition, ASM Press pp. 253-276 (1998).

Vaccination is a means of inducing the body's own immune system to seek out and destroy an infecting agent before it causes a pathological response. Typically, vaccines are either live, but attenuated, infectious agents (virus or bacteria) or a killed form of the agent. A vaccine consisting of a live bacteria or virus must be non-pathogenic. Typically, a bacterial or viral culture is attenuated (weakened) by physical or chemical treatment. Although the agent is nonvirulent, it can still elicit an immune response in a subject treated with the vaccine.

An immune response is elicited by antigens, either specific macromolecules, or an infectious agent. These antigens are generally either proteins, polysaccharides, lipids, or glycolipids, which are recognized as "foreign" by lymphocytes known as B cells and T cells. Exposure of both types of lymphocytes to an antigen elicits a rapid cell division and differentiation response, resulting in the formation of clones of the exposed lymphocytes. B cells produce plasma cells, which in turn, produce proteins called antibodies (Ab), which selectively bind to the antigens present on the infectious agent, thus neutralizing or inactivating the pathogen (humoral immunity). In some cases, B cell response requires the assistance of CD4 helper T cells.

The specialized T cell clone that forms in response to the antigen exposure is a cytotoxic T lymphocyte (CTL), which is capable of binding to and eliminating pathogens and tissues that present the antigen (cell-mediated or cellular immunity). In some cases, an antigen presenting cell (APC) such as a dendritic cell, will envelop a pathogen or other foreign cell by endocytosis. The APC then processes the antigens from the cells, and presents these antigens in the form of a histocompatibility molecule:peptide complex to the T cell receptor (TCR) on CTLs, thus stimulating an immune response.

Humoral immunity characterized by the formation of specific antibodies is generally most effective against acute bacterial infections and repeat infections from viruses, whereas cell-mediated immunity is most effective against viral infection, chronic intracellular bacterial infection, and fungal infection. Cellular immunity is also known to protect against cancers and is responsible for rejection of organ transplants.

Antibodies to antigens from prior infections remain detectable in the blood for very long periods of time, thus affording a means of determining prior exposure to a pathogen. Upon re-exposure to the same pathogen, the immune system effectively prevents reinfection by eliminating the pathogenic agent before it can proliferate and produce a pathogenic response.

The same immune response that would be elicited by a pathogen can also sometimes be produced by a non-pathogenic agent that presents the same antigen as the pathogen. In this manner, the subject can be protected against subsequent exposure to the pathogen without having previously fought off an infection.

Not all infectious agents can be readily cultured and inactivated, as is required for vaccine formation, however. Modern recombinant DNA techniques have allowed the engineering of new vaccines to seek to overcome this limitation. Infectious agents can be created that lack the pathogenic genes, thus allowing a live, nonvirulent form of the organism to be used as a vaccine. It is also possible to engineer a relatively nonpathogenic organism such as *E. coli* to present the cell surface antigens of a pathogenic carrier. The immune system of a subject treated with such a transformed carrier is "tricked" into forming antibodies to the pathogen. The antigenic proteins of a pathogenic agent can be engineered and expressed in a nonpathogenic species and the antigenic proteins can be isolated and purified to produce a "subunit vaccine." Subunit vaccines have the advantage of being stable, safe, and chemically well defined; however, their production can be cost prohibitive.

A new approach to immunization has emerged in recent years, broadly termed genetic immunization. In this approach, a gene encoding an antigen of a pathogenic agent is operably inserted into cells in the subject to be immunized. The treated cells are transformed and produce the antigenic proteins of the pathogen. These in vivo-produced antigens then trigger the desired immune response in the host. The genetic material utilized in such genetic vaccines can be either a DNA or RNA construct. Often the polynucleotide encoding the antigen is introduced in combination with other promoter polynucleotide sequences to enhance insertion, replication, or expression of the gene.

DNA compositions encoding antigens can be introduced into the host cells of the subject by a variety of expression systems. These expression systems include prokaryotic, mammalian, and yeast expression systems. For example, one approach is to utilize a viral vector, such as vaccinia virus incorporating the new genetic material, to innoculate the host cells. Alternatively, the genetic material can be incorporated in a vector or can be delivered directly to the host cells as a "naked" polynucleotide, i.e. simply as purified DNA. In addition, the DNA can be stably transfected into attenuated bacteria such as *Salmonella typhimurium*. When a patient is orally vaccinated with the transformed *Salmonella*, the bacteria are transported to Peyer's patches in the gut (i.e., secondary lymphoid tissues), which then stimulate an immune response.

DNA compositions encoding antigens provide an opportunity to immunize against disease states that are not caused by traditional pathogens, such as genetic diseases and cancer. Typically, in a genetic cancer vaccine, antigens to a specific type of tumor cell must be isolated and then introduced into the vaccine. An effective general vaccine against a number of cancers can thus entail development of numerous individual vaccines for each type of cancer cell to be immunized against.

One general approach to treatment of tumors involves administering angiogenesis inhibiting compounds to patients with growing tumors. Angiogenesis is the process by which new capillaries and blood vessels form. Angiogenesis is important in embryonic development, tissue growth, tissue repair, and tissue regeneration. In addition to these normal and essential processes, angiogenesis is also involved in many abnormal pathological processes such as tumor growth, tumor metastasis, and ocular vascular diseases such as diabetic retinopathy.

Angiogenesis involves a number of interdependent processes, including (a) activation of vascular endothelial cells, (b) decomposition of cell matrix proteins by endothelial cells expressing protease activity, (c) migration of endothelial cells to a potential growth sites, (d) proliferation of endothelial cells and (e) tube formation by differentiation of endothelial cells. Each of these processes is affected by a variety of promoter substances such as fibroblast growth factor (FGF), platelet-derived growth factor (PDGF), and vascular endothelial growth factors (VEGF). The vascular endothelial growth factors (collectively VEGF) play a crucial role in endothelial cell growth and differentiation. VEGF acts by binding to receptor protein-tyrosine kinases present in the endothelial cell membranes, which in turn initiate a cascade of signal transduction reactions that stimulate cell growth.

Inhibition of pathological angiogenesis has been proposed as a treatment for tumors. See, for example, Folkman et al. *Science*, 221, 719, (1983). The basic concept of such treatment is that, since tumors require vascularization to grow, inhibition of blood vessel formation, through the administration of angiogenesis inhibiting compounds, will prevent tumor growth by starving the tumor of its blood supply. A disadvantage of his approach is that angiogenesis inhibitors must be administered on a relatively continuous basis to prevent tumor growth. A cessation in delivery of the inhibitor can lead to a resumption of tumor growth. A DNA composition effective for eliciting an antiangiogenic immune response would be an attractive preventative agent against tumor formation.

There is a continuing need for a generally effective compositions for inhibiting angiogenesis and growth of a variety of tumors without the need for targeting specific tumor antigens. The present invention satisfies this need.

SUMMARY OF THE INVENTION

A DNA composition effective for inhibiting endothelial cell proliferation comprises a DNA construct that encodes a VEGF receptor polypeptide, which can be a full length VEGF receptor or an immunogenic fragment of a VEGF receptor, which is capable of eliciting an immune response against vascular endothelial cells, is expressible in immune cells, and is incorporated in a pharmaceutically acceptable carrier. VEGF receptors include VEGFR-2 (KDR; SEQ ID NO: 2), VEGFR-1 (Flt-1; SEQ ID NO: 4), and Flk-1 (SEQ ID NO: 6; the murine homolog of KDR), e.g., DNA sequences set forth in SEQ ID NO: 1, SEQ ID NO: 3, and SEQ ID NO 5, respectively. Preferably, immunogenic fragments of a VEGF receptor consist of about 8 to about 10 consecutive amino acid residues of a VEGF receptor.

The DNA compositions of the invention can encode a single immunogenic fragment of the VEGF receptor, a plurality of immunogenic fragments of the VEGF receptor in the form of a "minigene.", or an entire VEGF receptor. When the compositions encode two or more immunogenic fragments of a VEGF receptor, one fragment preferably is linked to another fragment in a linear manner, i.e., by a spacer peptide.

The DNA composition can comprise a linear nucleic acid such as a purified DNA construct, or a DNA construct incorporated in a plasmid vector. Preferably, the DNA construct is incorporated in an attenuated bacterial or viral vector in a manner such that the polypeptide encoded by the construct will be expressed in immune cells (e.g., macrophages and/or dendritic cells) within the subject to which the DNA composition has been administered. In this manner, the DNA compositions of the present invention stimulate formation of cytotoxic T lymphocytes (CTLs) active against proliferating endothelial cells that overexpress a VEGF receptor.

Endothelial cells form the lining of mammalian vascular tissue. The proliferation of endothelial cells is a key process in angiogenesis. The compositions of the present invention provide a method for producing long term inhibition of angiogenesis in an organism treated with the composition by eliciting an immune response against proliferating endothelial cells. Non-proliferating endothelial cells, such as the linings of established blood vessels, do not present significant quantities of VEGF receptor antigens, and thus remain substantially unaffected by the CTLs that are produced in response to the DNA compositions.

In a method aspect of the present invention, a DNA composition is utilized to provide long term inhibition of endothelial cell proliferation in a treated patient. In one method embodiment, a DNA composition (vaccine) comprising a polynucleotide construct encoding a VEGF receptor polypeptide is administered orally to a patient in need of inhibition of endothelial cell proliferation in an amount that is sufficient to elicit an immune response against proliferating endothelial cells.

The present invention also provides a method of inhibiting angiogenesis in a patient treated with a DNA composition of the invention. In such a method embodiment, an immune response eliciting amount of a DNA composition that includes a DNA construct encoding a VEGF receptor polypeptide is administered to a patient suffering from an angiogenesis-related disease.

In yet another method aspect of the present invention, tumor growth is inhibited by treating a patient with a DNA composition of the invention. In such a method embodiment, an immune response-eliciting amount of a DNA composition comprising a DNA construct operably encoding a VEGF receptor polypeptide is administered to a patient having a growing tumor. Administration of the composition results in tumor growth arrest. Destruction of proliferating endothelial cells by the patient's immune system prevents vascularization of the tumor, in essence starving the tumor to death.

In the method embodiments of the present invention, the DNA compositions can be administered enterally, such as by oral administration, or perenterally, such as by injection or intravenous infusion. The VEGF receptor polypeptide can be a full length VEGF receptor or an immunogenic fragment thereof.

The compositions of the present invention are useful for treatment and prevention of a number of disease states. For example, a patient suffering from a cancer, diabetic retinopathy, and the like, can benefit from immunization by the compositions of the present invention.

BRIEF DESCRIPTION OF THE DRAWINGS

In the Drawings,

FIG. 1 depicts the DNA sequence encoding human KDR, SEQ ID NO: 1.

FIG. 2 depicts the protein sequence of human KDR, SEQ ID NO: 2.

FIG. 3 depicts the DNA sequence encoding human Flt-1, SEQ ID NO: 3.

FIG. 4 depicts the protein sequence of human Flt-1, SEQ ID NO: 4.

FIG. 5 depicts the DNA sequence encoding mouse Flk-1, SEQ ID NO: 5.

FIG. 6 depicts the protein sequence of human Flk-1, SEQ ID NO: 6.

FIG. 12. (A) Schematic map: Minigenes encoding the murine H-2 Dd- and Kd-restricted Flk-1 nonapeptides and spacers were assembled by PCR with overlapping oligonucleotides as templates. The PCR fragments generated were cloned downstream of ubiquitin in a modified pcDNA expression vector by using Xho I and Xba I restriction sites. (B) Proteins encoded by minigenes were expressed in mammalian cells. 293 T cells were transfected separately with either pDd-myc, pDd+Kd1-myc, pKd-myc or pKd+Dd2-myc for 24 hours, harvested, lysed and analyzed by Western blotting with anti-myc monoclonal antibody.

FIG. 16. (A) Masson's trichrome staining of CT-26 lung metastasis tumor sections prepared 19 days after tumor cell challenge. The blue arrows indicate the blood vessels in the tumor. (B) Matrigel assay. Matrigel was implanted into mice vaccinated with either empty vector or pKd vaccines. Quantification of vessel growth by fluorimetry after staining of endothelium with FITC-labeled isolectin B4. The average fluorescence of Matrigel plugs from each group of mice is depicted by the bar graph (n=4; mean±SD). *, $P<0.05$ compared to empty vector control group.

DETAILED DESCRIPTION OF PREFERRED EMBODIMENTS

Figure 7:
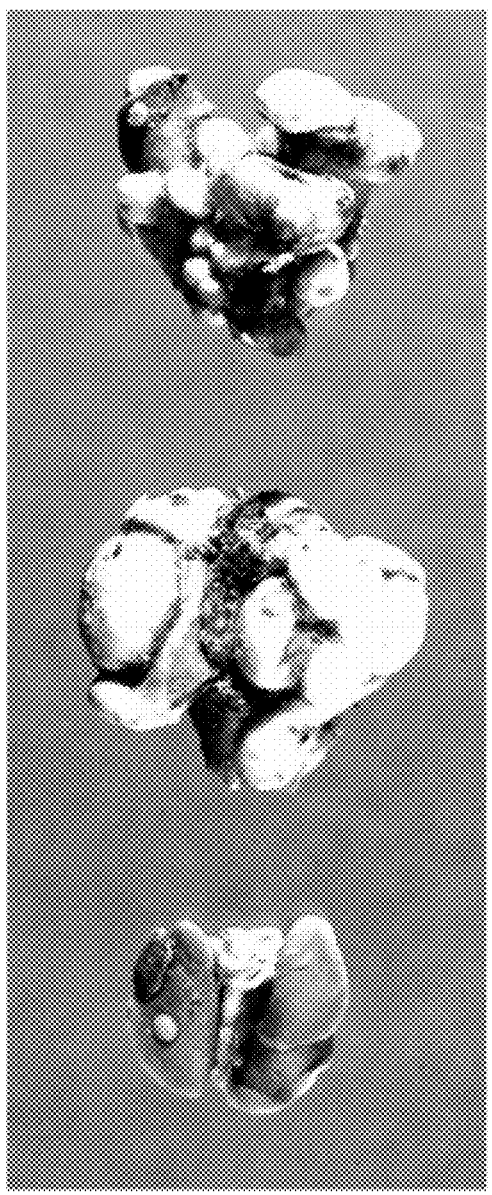
FIG. 7 is a pictorial representation of mouse lungs having varying levels of tumor coverage ranging from >50% coverage (labeled 3) to <10% coverage (labeled 1).

A DNA composition effective for inhibiting endothelial cell proliferation comprises a DNA construct that encodes a vascular endothelial growth factor (VEGF) receptor or at least one immunogenic fragment thereof capable of eliciting an immune response against vascular endothelial cells, incorporated in a pharmaceutically acceptable carrier. The VEGF receptor or immunogenic fragment thereof is expressible in immune cells. The term "DNA construct" as used herein and in the appended claims means a synthetic DNA structure that can be transcribed in target cells. The construct can comprise a linear nucleic acid, such as a purified DNA, or preferably, DNA incorporated in a plasmid vector. The DNA can also be incorporated in a viral or bacterial vector, preferably an attenuated viral or bacterial vector that is non-pathogenic. The DNA construct is capable of being expressed in immune cells (e.g., macrophages and/or dendritic cells) in a subject to which the DNA composition has been administered. As used herein and in the appended claims, the term "VEGF receptor polypeptide" includes full length VEGF receptors, as well as immunogenic fragments thereof, as described herein.

Suitable DNA constructs are those that encode a VEGF receptor such as VEGFR-2 (KDR; SEQ ID NO: 2), VEGFR-1 (Flt-1; SEQ ID NO: 4), and Flk-1 (SEQ ID NO: 6), e.g., DNA sequences SEQ ID NO: 1, SEQ ID NO: 3, and SEQ ID NO 5, respectively, or an immunogenic fragment (i.e., an epitope) thereof. Preferably, the DNA construct encodes two or more immunogenic VEGF receptor fragments linked together in linear fashion by a linker peptide between each fragment.

Five VEGF sub-types have been identified, including VEGF-1 (also known as VEGF-A), VEGF-2 (also known as VEGF-C), VEGF-B, VEGF-D and VEGF-E. See, for example, U.S. Pat. No. 6,235,713 to Achen et al. and references cited therein. VEGF receptors are protein-tyrosine kinases specific to endothelial cells. Several receptor protein-tyrosine kinases that are specific to endothelial cells have been identified, including Flt-1 (VEGF receptor 1; VEGFR-1), KDR (VEGFR-2), Flk-1 (the murine homolog of KDR), Flt-4 (VEGFR-3), Tie, Tie-2 and Tek, several of which are VEGF receptors.

Preferably, the compositions of the present invention comprise a DNA construct that encodes one or more VEGF receptor protein, such as a tyrosine kinase that is specific to endothelial cells, including, for example Flt-1, KDR, Flk-1, functional homologs thereof, or at least one immunogenic fragment (epitope) thereof. The functional homologs preferably share at least about 80% homology with the aforementioned VEGF receptor proteins. Immunogenic fragments of VEGF receptors preferably consist of about 8 to 10 contiguous amino acid resides from a VEGF receptor, i.e., from an epitope region of the protein.

In some preferred embodiments, the DNA construct encodes two or more (e.g., 2 to 5) immunogenic fragments of a VEGF receptor. The DNA construct preferably encodes the fragments linked together by a spacer peptide (e.g., AAA or AAY) between each fragment. Preferably, the DNA construct encoding an immunogenic fragment of a VEGF receptor also encodes a membrane-translocating peptide, such as the HIVtat peptide, connected to the N-terminus of the immunogenic fragment of legumain by a spacer peptide. When the DNA construct encodes two or more immunogenic fragments, the membrane-translocating peptide preferably is linked to the first fragment from the N-terminus thereof.

Immunogenic fragments of VEGF receptors can be identified by the HLA Binding Predictions program provided by the Bioinformatics & Molecular Analysis Section (BIMAS) of the National Institutes of Health (NIH) at the NIH www website, which is incorporated herein by reference.

The DNA compositions of the present invention stimulate formation of CTLs that are active against proliferating endothelial cells that overexpress a VEGF receptor. Because VEGF receptors are only substantially expressed on proliferating endothelial cells, a CTL that forms in response to contact with a composition of the invention will substantially target only tissues where active angiogenesis (e.g., vascularization) is occurring. Non-proliferating endothelial cells, such as the linings of established blood vessels, are substantially lacking in VEGF receptor antigens and are thus not affected by a CTL elicited by the DNA composition of the invention.

In a preferred embodiment, the DNA composition comprises a polynucleotide sequence that operably encodes at least one immunogenic fragment of a VEGF receptor incorporated in a vector capable of expressing the immunogenic fragment in an immune cell after being taken up by the immune cell. This composition can promote activation of naive T cells, both directly and indirectly, through the intervention of dendritic cells.

In some preferred embodiments, the DNA composition further comprises a DNA construct encoding an immune effector protein expressible in immune cells. As used herein and in the appended claims the phrase "immune effector protein" means a protein that is involved in regulation of an immune system pathway. Preferably, the immune effector protein is a cytokine Cytokines are proteins and polypeptides produced by cells that can affect the behavior of other cells, such as cell proliferation, cell differentiation, regulation of immune responses, hematopoiesis, and inflammatory responses. Cytokines have been classified into a number of families, including chemokines, hematopoietins, immunoglobulins, tumor necrosis factors, and a variety of unassigned molecules. See generally *Oxford Dictionary of Biochemistry and Molecular Biology*, Revised Edition, Oxford University Press, 2000; and C. A. Janeway, P. Travers, M. Walport and M. Schlomchik, *Immunobiology*, Fifth Edition, Garland Publishing, 2001 (hereinafter "Janeway and Travers"). A concise classification of cytokines is presented in Janeway and Travers, Appendix III, pages 677-679, the relevant disclosures of which are incorporated herein by reference.

Hematopoietins include, for example erythropoietin, interleukin-2 (IL-2, a 133 amino acid protein produced by T cells and involved in T cell proliferation), IL-3, IL-4, IL-5, IL-6, IL-7, IL-9, IL-11, IL-13, IL-15 (a 114 amino acid IL-2-like protein, which stimulates the growth of intestinal epithelium, T cells, and NK cells), granulocyte colony-stimulating factor (G-CSF), granulocyte-macrophage colony-stimulating factor (GM-CSF), oncostatin M (OSM), and leukemia inhibitory factor (LIF).

Interferons include, for example, IFN-α, IFN-β, and IFN-γ (a 143 amino acid homodimeric protein produced by T cells and NK cells, which is involved in macrophage activation, increased expression of MHC molecules and antigen processing components, IG class switching, and suppression of $T_H2$).

Immunoglobulins include, for example, B7.1 (CD80), and B7.2 (CD86), both of which co-stimulate T cell responses.

The tumor necrosis factor (TNF) family includes, for example, TNF-α, TNF-β (lymphotoxin), lymphotoxin-β (LT-β), CD40 ligands, Fas ligand, CD27 ligand, CD30 ligand, 4-1BB ligand, Trail, and OPG ligand.

The biological roles of CD40 ligand (CD40L), particularly its interaction with CD40 expressed on antigen presenting cells during costimulation of T cell activation, are well known in the art. CD40 is a 48 kDa glycoprotein expressed on the surface of all mature B cells, most mature B-cell malignancies, and some early B-cell acute lymphocytic leukemias, but it is not expressed on plasma cells, Clark, *Tissue Antigens* 1990, 35:33-36. CD40L, a type II membrane protein of about 35 kDa, is expressed on the surface of T cells upon antigen recognition. Members of the TNF family are biologically most active when expressed as homotrimers. CD40L is no exception in this regard and can be expressed as a homotrimer (CD40LT) by modification of a 33 amino acid leucine zipper motif fused to the N-terminus of the entire extracellular domain of this ligand. CD40LT DNA has been reported by Gurunathan et al. *J. Immunol.* 1998, 161:4563, to enhance cellular immune responses such as induction of IFN-γ and cytolytic T cell activity when mice were vaccinated with DNA encoding the highly immunogenic model antigen β-galactosidase.

CD40LT is an important factor in the activation of T cells necessary to induce an effective protective immunity against tumor self-antigens. Once MHC class I antigen:peptide complexes are taken up by dendritic cells (DCs) and presented to naive T cells, the first antigen signal is delivered via T cell receptors (TCR), followed by upregulation of CD40LT. On the T cell surface, CD40LT then induces costimulatory activity on DCs via CD40-CD40LT interactions. Thus primed, these APCs can express costimulatory molecules B7.1 (CD80) and B7.2 (CD86), which sends a second costimulatory signal to T cells via interaction with CD28, an event required for full activation of T cells to concurrently produce pro-inflammatory cytokines INF-γ and IL12, and to perform effector functions.

Various cytokines that are not assigned to a particular family include, for example, tumor growth factor-β (TGF-β), IL-1α, IL-1β, IL-1 RA, IL-10, IL-12 (natural killer cell stimulatory factor; a heterodimer having a 197 amino acid chain and a 306 amino acid chain, which is involved in NK cell activation and induction of T cell differentiation to $T_H1$-like cells), macrophage inhibitory factor (MIF), IL-16, IL-17 (a cytokine production-inducing factor, which induces cytokine production in epithelia, endothelia, and fibroblasts), and IL-18.

Chemokines are a family of cytokines that are relatively small chemoattractant proteins and polypeptides, which stimulate the migration and activation of various cells, such as leucocyte migration (e.g., phagocytes and lymphocytes). Chemokines play a role in inflammation and other immune responses. Chemokines have been classified into a number of families, including the C chemokines, CC chemokines, CXC chemokines, and $CX_3C$ chemokines. The names refer to the number and spacing of cysteine (c) residues in the molecules; C chemokines having one cysteine, CC chemokines having two contiguous cysteines, CXC having two cysteines separated by a single amino acid residue, and $CX_3C$ chemokines having two cysteines separated by three amino acid residues. Chemokines interact with a number of chemokine receptors present on cell surfaces. See Janeway and Travers, Appendix IV, page 680, which is incorporated herein by reference.

In addition, chemokines can have immunomodulating activity and have been implicated in immune responses to cancer. For example, murine 6Ckine/SLC, the mouse analog of the human secondary lymphoid tissue chemokine (SLC), now commonly referred to as CCL21, has been reported to induce an antitumor response in a C-26 colon carcinoma tumor cell line. See Vicari, et al. *J. Immunol.* 2000; 165(4): 1992-2000. Human CCL21 and its murine counterpart, 6Ckine/SLC, are classified as CC chemokines, which interact with the CCR7 chemokine receptor. Murine 6Ckine/SLC (muCCL21) is also reported by Vicari et al. to be a ligand for the CXCR3 chemokine receptor. Human CCL21, murine muCCL21 and a variety of other chemokines are implicated in the regulation of various immune system cells such as dendritic cells, T cells, and natural killer (NK) cells.

Mig and IP-10 are CXC chemokines that interact with the CXCR3 receptor, which is associated with activated T cells. Lymphotactin is a C chemokine, which interacts with the XCR1 receptor associated with T cells and NK cells. Fractalkine is a $CX_3C$ chemokine, which interact with the $CX_3CR1$ receptor that is associated with T cells, monocytes and neutrophils.

Particularly preferred immune effector proteins to be encoded by the DNA compositions of the present invention include cytokines IL-2 (a hematopoietin), CCL21 (a chemokine), as well as CD40 ligands such as CD40 ligand trimer (CD40LT), a TNF family cytokine.

DNA and protein sequences for human IL-2 have been published in GenBank, Accession No. BC070338, the disclosures of which are incorporated herein by reference. The DNA and protein sequences of murine IL-2 have been in GenBank, Accession No. NM 008366, the disclosures of which are incorporated herein by reference.

DNA and protein sequences for human CCL21 have been published in GenBank, Accession No. AB002409, the disclosures of which are incorporated herein by reference.

Human CD40 ligand (CD40L) is a 261 amino acid protein, which exists as a trimer (CD40LT) in its most active form. The DNA sequence encoding human CD40L (also known as CD154) has been published in GenBank, Accession No. NM 000074, the disclosure of which is incorporated herein by reference.

A DNA composition of the invention can be utilized to provide long term inhibition of tumor growth and/or tumor metastases in a patient treated with the composition. In a preferred embodiment, the DNA composition is administered in conjunction with an antitumor chemotherapeutic agent. The DNA composition can be administered together with the chemotherapeutic agent in a combined dosage form, or the composition and chemotherapeutic agent can be administered in separate dosage forms and at separate dosage intervals tailored to the pharmacology of the chemotherapeutic agent being administered.

Chemotherapeutic agents useful in combination with the DNA compositions of the present invention include antitumor agents such as doxorubicin, paclitaxol, a cyclophosphamide, etoposide, 5-fluorouracil, methotrexate, and the like.

As used herein, the term "immunity" refers to long term immunological protection against the virulent form of the infectious agent or tumor antigen. The term "immunization" refers to prophylactic exposure to an antigen of a pathogenic agent derived from a non-virulent source, which results in immunity to the pathogen in the treated subject.

A DNA composition of the present invention preferably comprises a nucleotide sequence that encodes a VEGF receptor or at least an immunogenic fragment of a VEGF receptor protein, operably linked to regulatory elements needed for gene expression in immune cells of the subject to be treated.

Useful DNA constructs preferably include regulatory elements necessary for expression of nucleotides. Such elements include, for example, a promoter, an initiation codon, a stop codon, and a polyadenylation signal. In addition, enhancers are often required for expression of a sequence that encodes an immunogenic target protein. As is known in the art, these elements are preferably operably linked to the sequence that encodes the desired polypeptide. Regulatory elements are preferably selected that are operable in immune cells of the subject to which they are to be administered.

Initiation codons and stop codons are preferably included as part of a nucleotide sequence that encodes the immunogenic fragment of the VEGF receptor protein in a DNA composition of the present invention. The initiation and termination codons must be in frame with the coding sequence.

Promoters and polyadenylation signals included in a composition of the present invention are preferably selected to be functional within the cells of the subject to be treated.

Examples of promoters useful in the compositions of the present invention, especially in the production of a composition for use in humans, include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, Cytomegalovirus (CMV) such as the CMV immediate early promoter, Epstein Barr Virus (EBV), Rous Sarcoma Virus (RSV) as well as promoters from human genes such as human actin, human myosin, human hemoglobin, human muscle creatine, and human metalothionein.

Examples of polyadenylation signals useful in the compositions of the present invention, especially in the production of a composition for humans, include but are not limited to SV40 polyadenylation signals and LTR polyadenylation signals.

In addition to the regulatory elements required for DNA expression, other elements can also be included in the DNA molecule. Such additional elements include enhancers. The enhancer can be, for example, human actin, human myosin, human hemoglobin, human muscle creatine and viral enhancers such as those from CMV, RSV and EBV.

Regulatory sequences and codons are generally species dependent, so in order to maximize protein production, the regulatory sequences and codons are preferably selected to be effective in the species to be immunized. One having ordinary skill in the art can produce DNA constructs that are functional in a given subject species.

The DNA constructs of the present compositions can be "naked" DNA as defined in Restifo et al. *Gene Therapy* 7, 89-92 (2000), the pertinent disclosure of which is incorporated by reference. Alternatively, the DNA can be operably incorporated in a vector. Useful delivery vectors include biodegradable microcapsules, immuno-stimulating complexes (ISCOMs) or liposomes, and genetically engineered attenuated live vectors such as viruses or bacteria.

Examples of suitable attenuated live bacterial vectors include *Salmonella typhimurium, Salmonella typhi, Shigella, Bacillus, Lactobacillus, Bacille Calmette-Guerin* (BCG), *Escherichia coli, Vibrio cholerae, Campylobacter*, or any other suitable bacterial vector, as is known in the art. Methods of transforming live bacterial vectors with an exogenous DNA construct are well described in the art. See, for example, Joseph Sambrook and David W. Russell, *Molecular Cloning, A Laboratory Manual*, 3rd Ed., Cold Spring Harbor Laboratory Press, Cold Spring Harbor, N.Y. (2001).

A preferred attenuated bacterial vector is an attenuated *Salmonella* carrier, which is the doubly attenuated strain of *S. typhimurium* designated as RE 88, and which includes the dam$^-$ and AroA$^-$ mutations, available from Remedyne Corporation (Goleta, Calif.). The attenuated *Salmonella* carrier is engineered to include DNA encoding a VEGF receptor polypeptide such as an immunogenic fragment of a VEGF receptor, which is expressible in immune cells of a mammal to which it is administered. The bacteria do not themselves express the immunogenic polypeptide, but rather deliver DNA encoding the polypeptide to immune cells, such as macrophages and dendritic cells (DCs), which in turn express the polypeptide. Such compositions can provide prolonged antitumor effects in murine models. Furthermore, in vivo depletion experiments of T cells indicated the involvement of CD8$^+$ but not CD4$^+$ T cells. The cytotoxic effect mediated by CD8$^+$ T cells in vitro is specifically directed against target proliferating endothelial cells that overexpress the VEGF receptors.

Preferred viral vectors include Bacteriophages, Herpes virus, Adenovirus, Polio virus, Vaccinia virus, and Avipox. Methods of transforming viral vector with an exogenous DNA construct are also well described in the art. See Sambrook and Russell, above.

Liposome vectors are unilamellar or multilamellar vesicles, having a membrane portion formed of lipophilic material and an interior aqueous portion. The aqueous portion is used in the present invention to contain the polynucleotide material to be delivered to the target cell. It is generally preferred that the liposome forming materials have a cationic group, such as a quaternary ammonium group, and one or more lipophilic groups, such as saturated or unsaturated alkyl groups having about 6 to about 30 carbon atoms. One group of suitable materials is described in European Patent Publication No. 0187702, and further discussed in U.S. Pat. No. 6,228,844 to Wolff et al., the pertinent disclosures of which are incorporated by reference. Many other suitable liposome-forming cationic lipid compounds are described in the literature. See, e.g., L. Stamatatos, et al., *Biochemistry* 27:3917-3925 (1988); and H. Eibl, et al., *Biophysical Chemistry* 10:261-271 (1979). Alternatively, a microsphere such as a polylactide-coglycolide biodegradable microsphere can be utilized. A nucleic acid construct is encapsulated or otherwise complexed with the liposome or microsphere for delivery of the nucleic acid to a tissue, as is known in the art.

The method aspects of the present invention comprise the step of administering DNA compositions of the invention to a mammal, such as a human. In some preferred embodiments, the DNA polynucleotides are administered orally, intramuscularly, intranasally, intraperitoneally, subcutaneously, intradermally, or topically.

In a method aspect of the present invention, a DNA composition of the invention can be utilized as a vaccine to provide long term inhibition of endothelial cell proliferation in a patient treated with the vaccine. In one preferred method embodiment, a DNA composition comprising a polynucleotide construct operably encoding a VEGF receptor polypeptide is administered to a mammal in need of inhibition of endothelial cell proliferation, in an amount that is sufficient to elicit an immune response against proliferating endothelial cells. The terms "DNA composition" and "DNA vaccine" are used interchangeably herein for convenience, with respect to the methods of the present invention.

The present invention also provides a method of inhibiting angiogenesis in a mammal treated with the DNA vaccine. In such a method embodiment, a vaccine comprising a DNA construct operably encoding a VEGF receptor polypeptide is administered to a mammal suffering from an angiogenesis related disease, in an amount sufficient to elicit an immune response against proliferating endothelial cells.

In yet another method aspect of the present invention, tumor growth is inhibited by treatment of a mammal with a DNA vaccine. In such a method embodiment, an immune response eliciting amount of a vaccine comprising a DNA construct operably encoding a VEGF receptor polypeptide is administered to a mammal having a growing tumor. Treatment with the vaccine results in tumor growth arrest by immunizing the mammal against proliferating endothelial cells. Destruction of proliferating endothelial cells by the mammal's immune system prevents, or at least minimizes vascularization of the tumor.

In the method embodiments of the present invention, the vaccines can be administered enterally, such as by oral administration, or by intramuscular injection. Preferably, the mammal treated with the inventive vaccine is a human. A patient suffering from cancer, such as lung or colon carcinoma, or prostate tumors, diabetic retinopathy, and the like, can benefit from immunization by the vaccines of the present invention.

Compositions of the present invention preferably are formulated with pharmaceutically acceptable carriers or excipients such as water, saline, dextrose, glycerol, and the like, and combinations thereof. The compositions can also contain auxiliary substances such as wetting agents, emulsifying agents, buffers, and the like.

The compositions of the present invention are preferably administered orally to a mammal, such as a human, as a solution or suspension in a pharmaceutically acceptable carrier, at a DNA concentration in the range of about 1 to about 10 micrograms per milliliter. The appropriate dosage will depend upon the subject to be vaccinated, and in part upon the judgment of the medical practitioner administering or requesting administration of the vaccine.

The compositions of the present invention can be packaged in suitably sterilized containers such as ampules, bottles, or vials, either in multi-dose or in unit dosage forms. The containers are preferably hermetically sealed after being filled with a compositions of the invention. Preferably, the compositions are packaged in a container having a label affixed thereto, which label identifies the compositions, and bears a notice in a form prescribed by a government agency such as the United States Food and Drug Administration reflecting approval of the vaccine under appropriate laws, dosage information, and the like. The label preferably contains information about the composition that is useful to an health care professional administering the compositions to a patient. The package also preferably contains printed informational materials relating to the administration of the composition, instructions, indications, and any necessary required warnings.

The amino acid sequences of VEGF receptor proteins have been disclosed in the art, as have the nucleic acid sequences encoding these proteins. The nucleic acid sequence encoding KDR (FIG. 1, SEQ ID NO: 1), and its corresponding protein sequence (FIG. 2, SEQ ID NO: 2) have been published by Yu et al., in the *EMBL* database of the European Bioinformatics Institute, Wellcome Trust Genome Campus, Hinxton, Cambridge CB10 1SD, UK (EMBL accession number is EMBL: AF063658), the disclosures of which are incorporated herein by reference. The nucleic acid sequence encoding Flt-1 (FIG. 3, SEQ ID NO: 3), and its corresponding protein sequence (FIG. 4, SEQ ID NO: 4) have been published by Yu et al., in the *EMBL* database of the European Bioinformatics Institute, Wellcome Trust Genome Campus, Hinxton, Cambridge CB10 1SD, UK (EMBL accession number is EMBL: AF063657), the disclosures of which are incorporated herein by reference.

The nucleic acid sequence encoding Flk-1, and its corresponding protein sequence have been published by Mathews et al., *Proc. Natl. Acad. Sci. USA* 1991, 88:9026-9030, and the structures were corrected by Quinn et al., *Proc. Natl. Acad. Sci. USA* 1991, 90:7533-7537, the relevant disclosures of which are incorporated herein by reference. The corrected DNA sequence of Flk-1 is provided in FIG. 5 as SEQ ID NO: 5, and the corrected protein sequence of Flk-1 is provided in FIG. 6 as SEQ ID NO:6.

Due to the inherent degeneracy of the genetic code, other DNA sequences which encode substantially the same or a functionally equivalent amino acid sequence to VEGF receptor proteins such as KDR, Flk-1 and Flt-1, can be used in the practice of the invention. Such DNA sequences include those which are capable of hybridizing to the VEGF receptor sequences as well. Preferably the functionally equivalent homologs of the VEGF receptor protein DNA shares at least about 80% homology with the DNA encoding the aforementioned VEGF receptor proteins.

Altered DNA sequences which can be used in accordance with the invention include deletions, additions or substitutions of different nucleotide residues resulting in a sequence that encodes the same or a functionally equivalent gene product. The gene product itself may contain deletions, additions or substitutions of amino acid residues within the VEGF receptor sequences, which result in a silent change, thus producing a functionally equivalent VEGF receptor proteins. Such amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine. As used herein, a functionally equivalent VEGF receptor refers to a receptor that binds to VEGF or fragments thereof, but not necessarily with the same binding affinity of its counterpart native KDR, Flk-1 or Flt-1.

The DNA constructs may be engineered in order to alter the VEGF receptor coding sequence for a variety of ends including, but not limited to, alterations that modify processing and expression of the gene product. For example, mutations may be introduced using techniques that are well known in the art, e.g. site-directed mutagenesis, to insert new restriction sites, to alter glycosylation patterns, phosphorylation, etc.

Mouse Flk-1 (SEQ ID NO: 6) shares an approximately 85% homology with human KDR (SEQ ID NO: 2) and plays an analogous role in mouse physiology to the role of KDR in humans. In fact, VEGFR-2 is often referred to as KDR/Flk-1, reflecting the close analogy between these two VEGF receptor homologs. For this reason, treatment of mice with a DNA vaccine of the invention, encoding Flk-1 (e.g., DNA SEQ ID NO: 5) was chosen as a suitable model for human DNA vaccines encoding KDR.

The following examples are provided to further illustrate the features and embodiments of the present invention, and are not meant to be limiting.

MATERIALS, METHODS AND EXAMPLES

Materials. C57/BL/6J and Balb/C mice were obtained from the Scripps Research Institute breeding facility. The murine tumor cell lines used for evaluation included the melanoma cell line B16 and the colon carcinoma cell line CT26, all of which were obtained from Dr. I. J. Fidler, MD Anderson Cancer Center, Houston, Tex. The murine Lewis lung cancer cell line D121 was obtained from Dr. Lea Eisenbach, Weizmann Institute, Rehovot, Israel. The DNA encoding Flk-1 was kindly provided by Dr. Lemischka (Princeton University, Princeton, N.J.), and was cloned into the pcDNA3.1 eucaryotic expression vector provided by Invitrogen, Huntsville, Ala., using the restriction sites KpnI and XbaI. An attenuated strain of *Salmonella typhimurium* was provided by B. A. D. Stocker (Stanford University, Stanford, Calif.). Antibodies were obtained from BD Biosciences, Bedford, Mass. T-STIM culture supplement was obtained from BD Biosciences, Bedford, Mass. Fluorescein isothiocyanate (FITC) and R-Phycoerythrin (PE) were obtained from Molecular Probes, Eugene, Oreg. FITC-labeled and PE-labeled antibodies were prepared according to the manufacturer's recommended protocols.

EXAMPLE 1

Preparation of a DNA Vaccine Encoding Flk-1

The pcDNA3.1 vector containing Flk-1 DNA (SEQ ID NO: 5; about 10 pg to about 0.1 µg of pDNA) was electroporated into freshly prepared attenuated *Salmonella typhimurium*, utilizing a Bio-Rad Pulser at 2.5 kV, 25 µF, and 200 Ohm according to the manufacturer's recommended procedures. *Salmonella* containing the vector were selected on ampicillin-containing plates. Colonies were picked the next day and cultured overnight in LB broth (EM Science, Gibbstown, N.J.) with ampicillin added. The bacteria were isolated and washed in phosphate buffered saline (PBS). The washed bacteria were then suspended in PBS medium at a concentration of about 1×10⁹ recombinant *Salmonella* per milliliter of PBS, to form a vaccine solution for later use. The vaccine was stored in sealed ampules until used. A "control vaccine" consisting of *Salmonella* transformed with the pcDNA3.1 vector alone (no Flk-1 DNA) was also prepared according to the same procedure. The plasmid DNA was stored at about −80° C. before transforming the *Salmonella*.

EXAMPLE 2

Vaccination of Mice with a DNA Vaccine Encoding Flk-1

Balb/C mice (about 6 mice per treatment group) were vaccinated with the DNA vaccine of Example 1 (about 1×10⁸ recombinant *Salmonella* in about 100 µl of PBS) by oral gavage, three times at two week intervals. Another group of mice were vaccinated with control vaccine (consisting of attenuated *Salmonella* containing the empty vector) according to the same schedule as the mice vaccinated with the inventive vaccine.

EXAMPLE 3

Evaluation of Tumor Resistance of Vaccinated Mice

About two weeks after the third vaccination, Balb/C mice from Example 2 (about 6 mice per treatment group) were challenged with either about 1×10⁵ B16 melanoma cells (subcutaneously), about 1×10⁵ D121 Lewis lung carcinoma cells (subcutaneously), or about 7.5×10⁴ CT26 colon carcinoma cells (intravenously). The subcutaneous Lewis lung tumors were surgically removed after about two weeks of growth to allow spontaneous dissemination to the lung. Subcutaneous tumor growth was measured in two dimensions every other day, and tumor volume was calculated according to the formula:

$$\text{volume} = (\text{width}^2)(\text{length} \div 2)$$

for each tumor. The amount of spontaneous metastasis of D121 to the lungs was evaluated about 30 days after removal of the subcutaneous primary tumor. The mice were sacrificed and necropsied, and the tumor burdens of the lungs were evaluated according to the percentage of the lung surface that was covered by tumor and scored as "0" for no tumor, "1" for less than about 20% tumor coverage, "2" for about 20 to about 30% tumor coverage, and "3" for greater than about 50% tumor coverage. FIG. 7 shows pictures of lungs from three mice challenged with D121 Lewis lung carcinoma cells. The lower lung was scored 1, whereas the upper two lungs were scored 3, having a large proportion of the lung surface covered by tumors. Animals that died prior to the 30 day evaluation were given a "+" score.

The results of these evaluations are provided in Tables 1-4, and in FIGS. 8-10, discussed in detail below.

TABLE 1

Tumor Metastasis in Balb/C Mice Challenged with D121 Lewis Lung Carcinoma Cells.

| Mouse Vaccination Group | Metastatic Scores |
| --- | --- |
| Control - vaccination with untransformed Salmonella | 3,3,3,3,+,+ |
| Control - vaccination with control vaccine (containing empty vector) | 3,3,3,3,+,+ |

TABLE 1-continued

Tumor Metastasis in Balb/C Mice Challenged with D121 Lewis Lung Carcinoma Cells.

| Mouse Vaccination Group | Metastatic Scores |
| --- | --- |
| Vaccination with DNA Vaccine of Example 1 (containing Flk-1) | 0,0,1,1,1,2,2 |

The Balb/C mice that were challenged by intravenous injection of CT-26 colon carcinoma cells were evaluated for mortality over about a 63 day (7 week) period. Mortality information is presented in Table 2 below, and graphically illustrated in FIG. 8.

Figure 8:
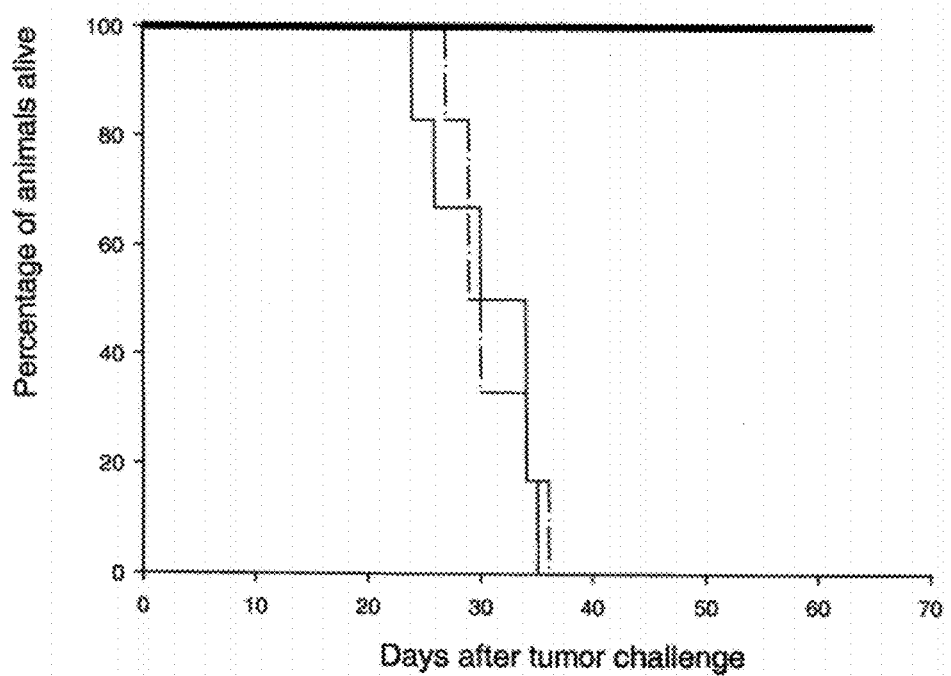
FIG. 8 is a graphical representation of data demonstrating that mice treated with a DNA composition encoding a VEGFR polypeptide (solid, heavy black line) and challenged by intravenous injection of CT-26 colon carcinoma cells, exhibited significantly reduced mortality relative to two control groups of mice (naive mice: solid thin line; control: dash-dot line).

In FIG. 8, the % survival of mice treated with the inventive vaccine of Example 1 is indicated by the heavy, solid line at 100% survival. The % survival of naive mice (no vaccination) challenged with the C26 cell is indicated by the solid, thin line, whereas, the % survival of the mice treated with the control vaccine (no Flk-1 DNA) is indicated by the dot-dash line.

TABLE 2

Suppression of Mortality in Balb/C Mice Immunized With the Vaccine of Example 1 and Challenged with CT 26 Carcinoma.

| Treatment | % Survival on Day 30 | % Survival on Day 36 | % Survival on Day 63 |
| --- | --- | --- | --- |
| Control, No Vaccine | 50 | 0 | 0 |
| Control Vaccine | 33 | 0 | 0 |
| Vaccine of Ex. 1 | 100 | 100 | 100 |

The suppression of growth of the primary (subcutaneous) tumor in D121 challenged Balb/C mice was evaluated by determination of primary tumor volume at day 14 after challenge. Results are presented in Table 3 below, and graphically illustrated in FIG. 9.

Figure 9:
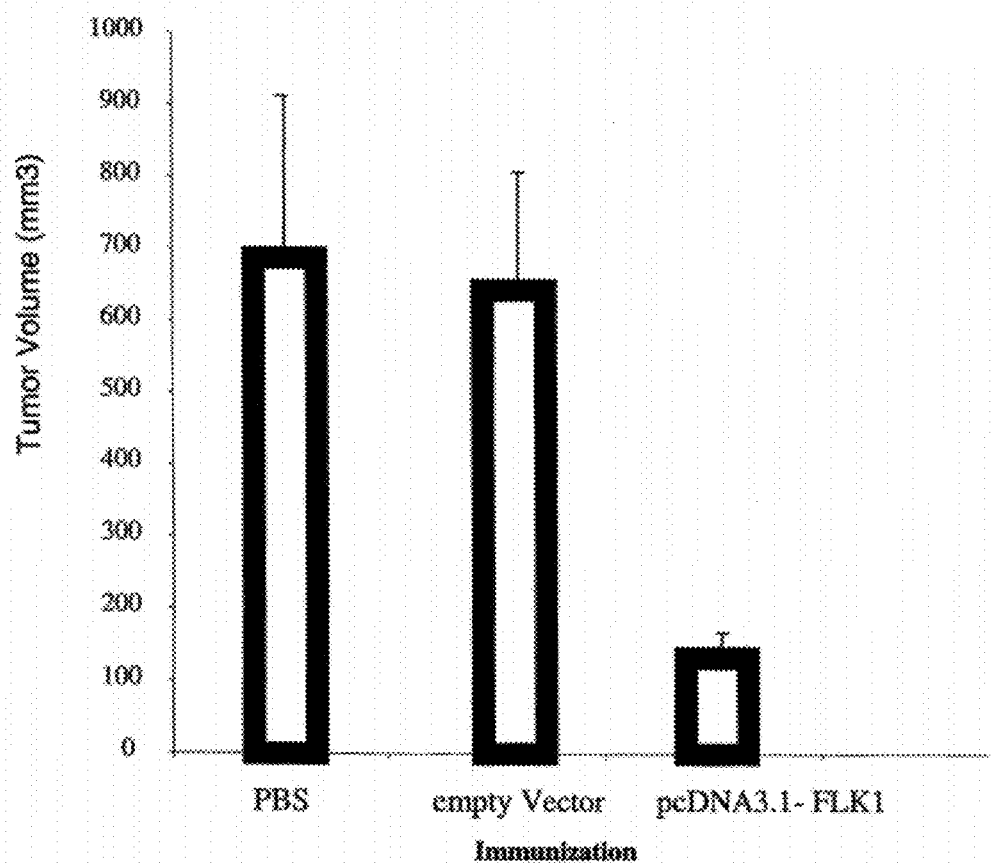
FIG. 9 is a graphical representation of data demonstrating the suppression of D121 Lewis lung carcinoma tumor growth in mice treated with a DNA composition encoding a VEGFR polypeptide (pcDNA3.1-FLK-1) relative to two control groups of mice.

In FIG. 9, the first bar, labeled "PBS" indicates mice that were not vaccinated (naive mice), the middle bar, labeled "empty vector" indicates mice treated with the control vaccine, and the third bar, labeled "pcDNA3.1-Flk1" indicates mice immunized with the inventive vaccine of Example 1.

TABLE 3

Suppression of Subcutaneous D121 Carcinoma Tumor in Balb/C Mice Immunized With the Vaccine of Example 1.

| Treatment | Tumor volume mm³ | Standard Deviation |
| --- | --- | --- |
| Control No Vaccine | 665 | 227 |
| Control Vaccine | 641 | 157 |
| Vaccine of Ex. 1 | 183 | 35 |

Suppression of subcutaneous B16 melanoma tumor growth was evaluated by monitoring the subcutaneous tumor volume over a period of about 17 days after tumor challenge. Results are presented in Table 4 and graphically illustrated in FIG. 10 below. In FIG. 10, average tumor volume data indicated by (●) represents mice immunized with the inventive vaccine of Example 1, whereas data indicated by (○) indicates mice treated with the control vaccine.

TABLE 4

Suppression of Subcutaneous B16 Melanoma Tumor in
Balb/C Mice Immunized With the Vaccine of Example 1.

|  | Tumor Volume (mm³) on Day | | | |
|---|---|---|---|---|
| Treatment | 0 | 9 | 14 | 17 |
| Control Vaccine | 0 | 907 | 1273 | 4213 |
| Vaccine of Ex. 1 | 0 | 447 | 462 | 1063 |
| % Tumor Suppression | — | 51% | 64% | 75% |

EXAMPLE 4

Upregulation of CD25, CD69 and CD2 Activation Markers in Splenocytes (CD8+ T Cells) from Vaccinated Mice C5/7BL/6J mice (about 4 mice per treatment group) were vaccinated with the DNA vaccine of Example 1 and the control vaccine (no Flk-1) as described in Example 2. Splenocytes were isolated from the immunized mice and the control mouse group about six weeks after the third vaccination. The splenocyte cells were cultured for 24 hours together with cells from a B16 melanoma cell line transduced to express Flk-1 and with untransformed B16 cells in T cell medium (about 5 mL per culture) containing about 4% by volume of T-STIM culture supplement (Cat. #354115, BD Biosciences, Bedford, Mass.). The cells were then stained with FITC-conjugated CD8+ antibody and PE-conjugated antibodies of CD25, CD69, and CD2. The cell suspensions were evaluated using a Becton Dickenson FAC scan to determine the percentage of CD8+ T cells positive for CD25 and CD69 for each splenocyte/B16 melanoma cell combination. The results are presented in Table 5 and are illustrated graphically in FIG. 11.

TABLE 5

Upregulation of CD25, CD69 and CD2 Activation
Markers in Splenocytes From Vaccinated Mice

| Treatment | % CD25 positive | % CD69 positive | CD2 positive mean fluorescence |
|---|---|---|---|
| Control vaccine + B16-Flk-1 cells | 9 | 18 | 570 mfu |
| DNA vaccine + B16 cells | 12 | 29 | 550 mfu |
| DNA vaccine + B16-Flk-1 cells | 21 | 35 | 700 mfu | mfu = mean fluorescence units.

The results provided in Tables 1-5 and FIGS. 8-11 demonstrate that the DNA vaccine of Example 1, comprising a DNA encoding Flk-1, the murine analog of KDR, can effectively immunize mice against a variety of tumor forming cancer cells. Although not intending to be bound by theory, it is believed that the vaccine acts by inhibiting angiogenesis in the tumor, i.e., preventing new blood vessel formation and effectively starving the tumor.

The data in Table 1 demonstrate that the inventive vaccine of Example 1 leads to a suppression of tumor metastasis to the lungs of mice challenged with D121 Lewis lung carcinoma. None of the mice immunized with the vaccine of Example 1 died, and all had less than about 50% tumor coverage on the lungs (2 had <20%). In contrast, two mice died from each control group and all of the remaining mice had greater than about 50% tumor coverage on the lungs.

The inventive vaccine of Example 1 also significantly decreased mortality of Balb-C mice that were challenged intravenously by CT-26 colon carcinoma cells, as demonstrated by the data in Table 2 and FIG. 8. All of the mice immunized with the vaccine of Example 1 survived the entire 63 day observation period after challenge. In the control groups, however, all of the mice had died by day 36 post challenge.

As demonstrated by the data in Table 3 and FIG. 9, subcutaneous D121 Lewis lung carcinoma tumor growth was suppressed by immunization with the inventive vaccine of Example 1 by a factor of about 4.3 to about 4.5, relative to the control mouse groups treated with no vaccine or the control vaccine.

Figure 10:
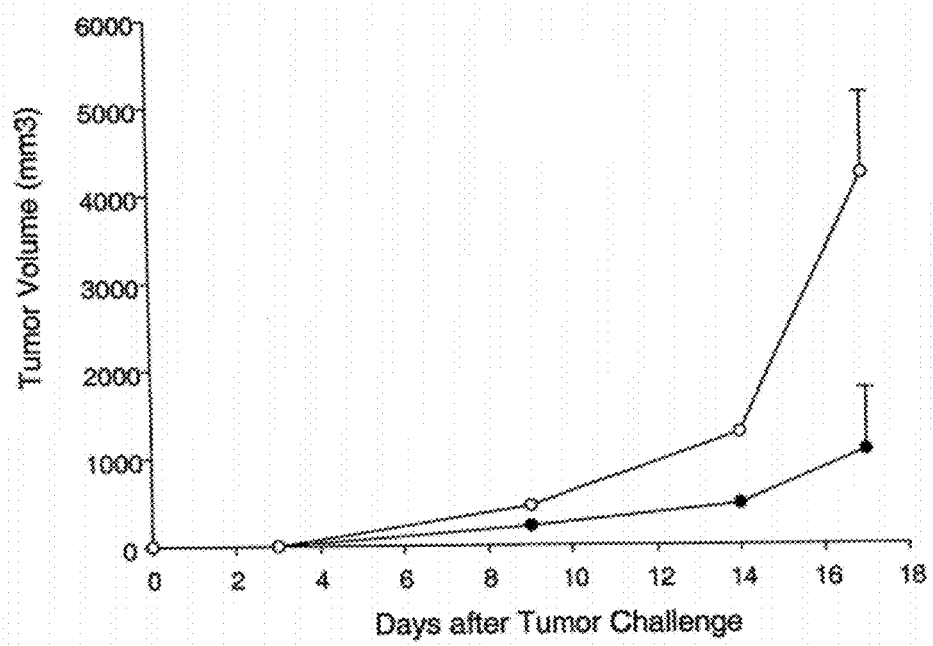
FIG. 10 is a graphical representation of data demonstrating the suppression of B16 melanoma tumor growth in mice vaccinated with a DNA composition encoding a VEGFR protein (●) relative to a control group (○).

Similarly, as shown in Table 4 and FIG. 10, subcutaneous B16 melanoma tumor growth was suppressed by a factor of about 4 in mice immunized with the inventive vaccine of Example 1, relative to tumor growth in the control group.

Figure 11:
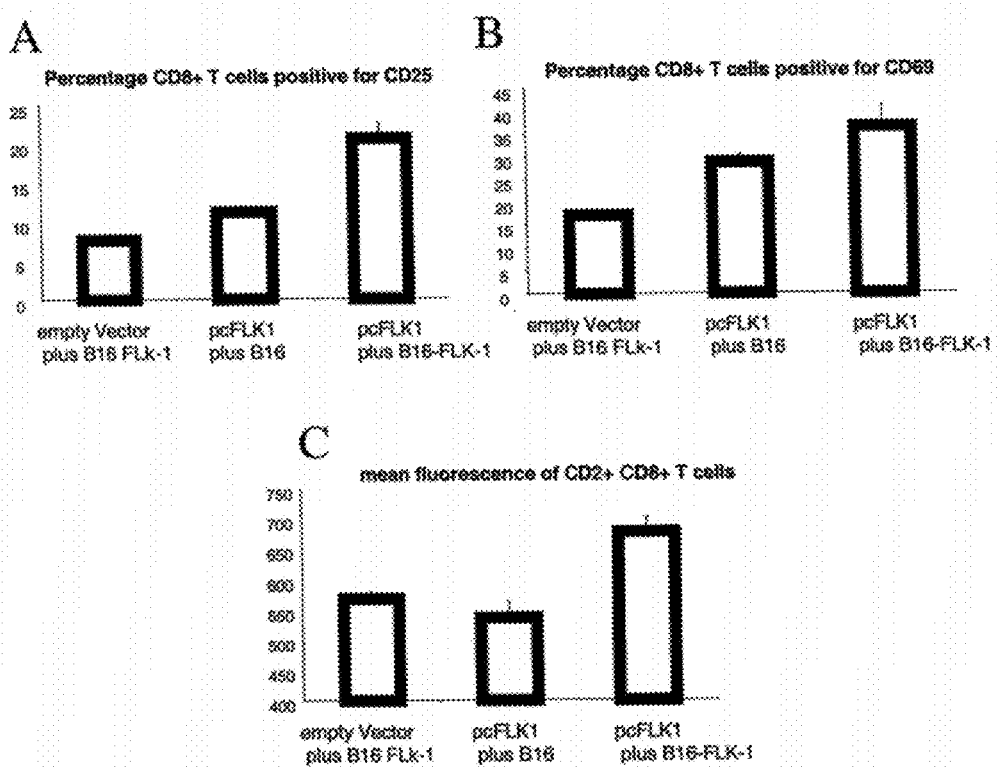
FIG. 11 is a graphical representation of data demonstrating the upregulation of CD25, CD69, and CD2 positive CD8+ T cells in mice treated with a DNA composition encoding a VEGFR polypeptide relative to a control group of mice.

The data in Table 5 and FIG. 11 show that splenocytes isolated from C57/BL/6J mice vaccinated with the DNA vaccine of Example 1 exhibited an upregulation of CD2, CD25 and CD69 activation markers relative to the control group of mice, when cultured with B16 melanoma cells transformed to present Flk-1 antigen.

The following additional non-limiting Examples further illustrate the compositions and methods of the present invention in which the VEGF receptor polypeptide is an immunogenic fragment of a VEGF receptor.

EXAMPLE 5

DNA Composition Encoding Immunogenic Fragments of a VEGF Receptor and Evaluation Therefor in a BALB/c Mouse Model Animals, Bacterial strains, and cell lines: Female BALB/c mice were purchased from the Jackson Laboratory. All animal experiments were performed according to the National Institutes of Health Guide for the Care and Use of Laboratory Animals. The murine D2F2 breast cancer cell line was kindly provided by Dr. W.-Z. Wei (Karmanos Cancer Institute, Detroit, Mich., USA). The murine colon carcinoma cell line CT-26 was provided by Dr. I. J. Fidler (MD Anderson Cancer Center, Houston, Tex.). The murine high endothelial venule cell line (HEVc) was a gift from Dr. J. M. Cook-Mills (University of Cincinnati, Ohio, USA). The HEVc-Flk-1 cell line was established by retroviral transduction with the Flk-1 gene by Drs. Harald Wodrich and Andreas G. Niethammer. The doubly attenuated *S. typhimurium* (AroA-, dam-) strain RE88 was kindly provided by Remedyne Corporation (Santa Barbara, Calif.) and was transduced with DNA vaccine plasmids to serve as a vaccine carrier, as described above.

Construction of Expression Vectors. Vector construction is illustrated schematically by FIG. 12, Panel A. The expression vectors were established based on the pcDNA/Myc/His vector (Invitrogen, Carlsbad, Calif.) containing the ubiquitin sequence. The peptides were cloned downstream of ubiquitin, and the sequence of each peptide is indicated in Table 6. All peptides were engineered to be in-frame with the myc epitope. Constructs were confirmed by DNA sequencing at The Scripps Research Institute's Core Facility (La Jolla, Calif.). Peptide expression was demonstrated by Western blotting analysis of transfected 293 T cells with monoclonal anti-myc antibody (Invitrogen). Once peptide expression was verified, a stop codon was introduced immediately in front of the myc epitope sequences. The resulting vectors, pDd, pKd, pDd+Kd1, and pKd+Dd2 were each verified by nucleotide sequencing and used to transform doubly attenuated *S. typhimurium* (dam-, AroA-) for subsequent immunization.

TABLE 6

Immunogenic Flk Fragments.

| Peptide Name | Sequence | SEQ ID NO: | Included in vaccine |
|---|---|---|---|
| Flk$_{54}$ | RGQRDLDWL | 7 | pDd; pDd + Kd1 |
| Flk$_{210}$ | TYQSIMYIV | 8 | pKd; pKd + Dd2 |
| Flk$_{221}$ | VGYRIYDVI | 9 | pDd; pKd + Dd2 |
| Flk$_{366}$ | WYRNGRPIE | 10 | pKd; pDd + Kd1 |
| Flk$_{438}$ | QYGTMQTLT | 11 | pKd: pKd + Dd2 |
| Flk$_{741}$ | LGCARAETL | 12 | pDd; pDd + Kd1 |
| Flk$_{792}$ | EGELKTGYL | 13 | pDd; pKd + Dd2 |
| Flk$_{993}$ | LYKDFLYTE | 14 | pKd; pDd + Kd1 |
| Flk$_{1147}$ | QRPSFSELV | 15 | pDd; pDd + Kd1 |
| Flk$_{1153}$ | ELVEHLGNL | 16 | pKd; pKd + Dd2 |

Oral Immunization and Tumor Cell Challenge. Groups of BALB/c mice were immunized 3 times at 1-week intervals by gavage with 100 μl PBS containing approximately 5×10$^8$ CFU of RE88 *S. typhimurium* harboring either empty vector, pDd, pKd, pDd+Kd1 and pKd+Dd2 plasmids. Mice were challenged i.v. with different carcinoma cell lines 2 weeks after the last immunization.

Cytotoxicity Assay. Cytotoxicity was measured by a standard $^{51}$Cr-release assay as previously described (Zhou, H. et al. *J. Clin. Invest.*, 2004; 113: 1792-1798). The percentage of specific target cell lysis was calculated by the formula [(E−S)/(T−S)]×100, where E is the average experimental release, S is the average spontaneous release, and T is the average total release.

Evaluation of anti-angiogenic activity. Suppression of angiogenesis was determined by the Matrigel assay as previously described (Niethammer et al. *Nat. Med.*, 2002, 8: 1369-1375). Vessel growth in the Matrigel was determined with fluorimetry by staining the endothelium using FITC-labeled isolectin B4.

Statistical Analysis. The statistical significance of differential findings between experimental groups and controls was determined by Student's t test. Findings were regarded as significant, if two-tailed P values were <0.05.

Results.

Minigenes encoded by expression vectors are expressed in mammalian cells. As shown in the previous examples, a DNA composition encoding the entire murine Flk-1 gene effectively induced CD8 T cell-mediated anti-angiogenesis that protected mice from tumor cell challenges. This example demonstrates that DNA compositions encoding an immunogenic fragment of a VEGF receptor also elicit an effective antitumor response. Five peptides were included in H-2 Dd- or H-2 Kd-restricted minigenes based on the binding predicted for these MHC class 1 molecules by the HLA Peptide Binding Predictions program provided by the BioInformatics & Molecular Analysis Section (BIMAS) of NIH, website. The amino acid sequences of these peptides are listed in Table 6.

Expression vectors were constructed based on the backbone of pcDNA/myc/His (FIG. 12, Panel A) that was modified to encode ubiquitin. Ubiquitin is useful for effective antigen processing in the proteasome leading to efficacious minigene vaccines. Gene expression of the resulting plasmids was verified by Western blotting analysis of 293 T cells transfected with either pDd-myc, pDb+Kd1-myc, pKd-myc or pKd+Dd2-myc. As expected, 293 T cells transfected with pKd-myc or pKd+Dd2-myc plasmid displayed two major bands of approximately 12 and 21 Kda, corresponding to non-ubiquitinated or ubiquitinated polypeptides, respectively (FIG. 12, Panel B). However, Western Blot analysis of 293 T cells transfected with pDd-myc and pDd+Kd1-myc showed bands of slightly higher molecular weight with the upper band being a doublet. Since these plasmids contain the correct nucleotide sequences, this phenomenon is indicative of post-translational modification, likely glycosylation. According to glycosylation prediction based on the program provided by Center for Biological Sequence Analyses at the Technical University of Denmark (DTU), website, the S$_{1150}$ and S$_{1152}$ amino acid residues in the Flk$_{1147}$ peptide (Table 6), which were included in the pDd-myc and pDd+Kd1-myc vectors, are most likely to be glycosylated, with S$_{1152}$ being almost 10 times more likely to be glycosylated than all other residues encoded by these minigenes.

The vectors pDd, pKb, pDd+Kd1 and pKd+Dd2 were generated by introducing a stop codon immediately downstream from the peptide coding sequences, so that the translated protein would not contain the myc epitope. The correct constructs were confirmed by DNA sequencing. The empty pcDNA vector was also included for control purposes, since previous data indicated that vectors containing only ubiquitin did not induce any tumor protective immune responses.

Figure 13:
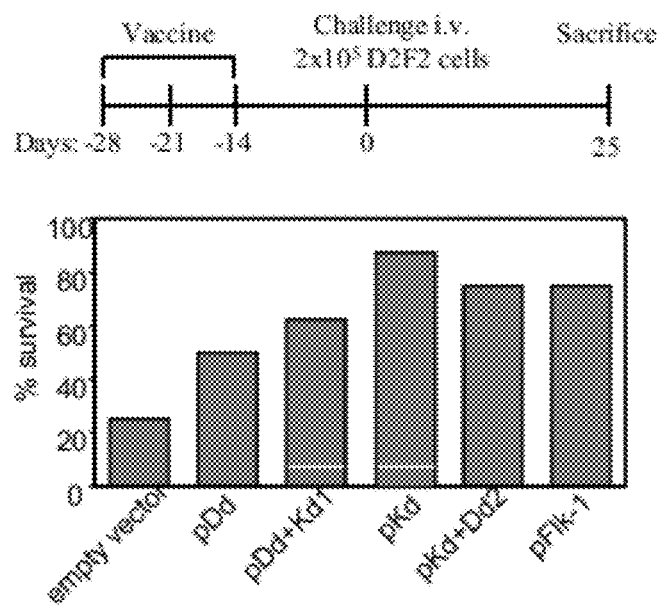
FIG. 13. Top panel: Schematic of experimental protocol. Lower panel: Survival rate of mice 25 days after tumor cell challenge. The Flk-1 whole gene vaccine was used as positive control. Groups of BALB/c mice (n=8) were immunized 3 times at 1 week intervals with attenuated Salmonella typhimurium RE-88 harboring the vectors indicated. Mice were challenged 2 weeks after the last immunization by i.v. injection of $2\times10^5$ D2F2 breast carcinoma cells.

The minigene vaccines protect mice against tumors of different origin. Initially, the minigene DNA vaccines were tested in a breast carcinoma model, where mice were first vaccinated with the minigene vaccines and then challenged i.v. with murine D2F2 breast carcinoma cells (FIG. 13, upper panel). In the empty vector control group, only 25% of the mice survived 25 days after tumor cell challenge (FIG. 13). In contrast, the survival rate was 50% and 62.5% in pDd and pDd+Kd1 vaccinated groups, respectively. More importantly, the survival rate improved to 82.5% and 75% in pKd and pKd+Dd2 vaccinated groups of mice, respectively. This is quite comparable to the 75% survival rate which was observed in groups of mice immunized with the whole Flk-1 gene vaccine (FIG. 13).

Figure 14:
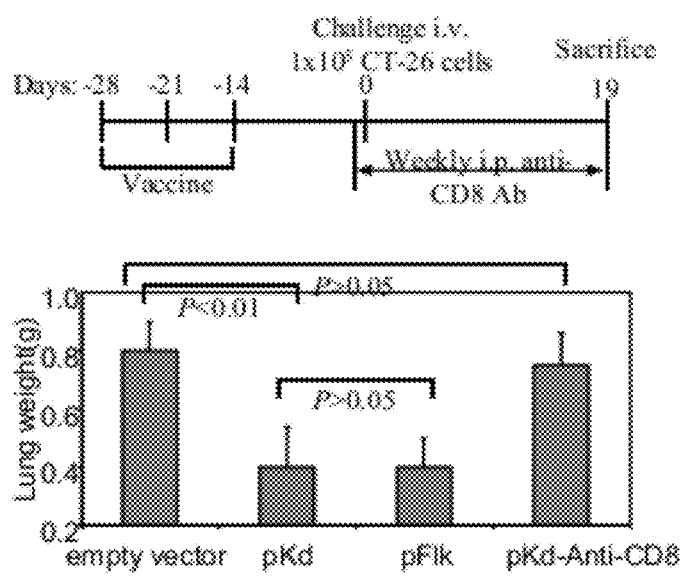
FIG. 14. Top panel: Schematic of experimental protocol. Lower panel: Average lung weights of mice from each experimental group 19 days after tumor cell challenge. The average lung weight of normal mice was about 0.2 g. The Flk-1 whole gene vaccine was used as positive control. Groups of BALB/c mice (n=8) were immunized 3 times at 1 week intervals with attenuated Salmonella typhimurium harboring the vectors indicated. Mice were challenged 2 weeks after the last immunization by i.v. injection of $1\times10^5$ CT-26 colon carcinoma cells. CD8 depletion was performed by i.p. injections of anti-CD8 antibody (2.43, 0.5 mg/mouse) 1 day before tumor challenge, and repeated weekly injections.

To verify that the minigene vaccine designed for anti-angiogenesis is not merely specific for D2F2 breast carcinoma, its efficacy was also tested in the CT-26 murine colon carcinoma model. In this case, this pKd minigene also decreased the tumor load by 60% (FIG. 14). Similar results were also obtained by using full-length Flk-1 DNA vaccine (FIG. 14). Taken together, these data demonstrate that Flk-1 minigene vaccines also elicit protections against tumors of different origin in syngeneic BALB/c mice.

The minigene vaccines induce a CTLs response which is capable of killing Flk-1$^+$ endothelial cells. To identify the effector cell population responsible for the vaccine induced tumor protection, in vivo depletion experiments were performed. CD8 T cells were depleted by i.p. injection of 0.5 mg/mouse 2.43 anti-CD8 monoclonal antibody 1 day before tumor cell challenge and repeated weekly (FIG. 14, upper panel). The depletion of CD8 T cells completely abrogated the pKd minigene-induced tumor protection (FIG. 14), indicating that CD8 T cells are the major effector cells.

Figure 15:
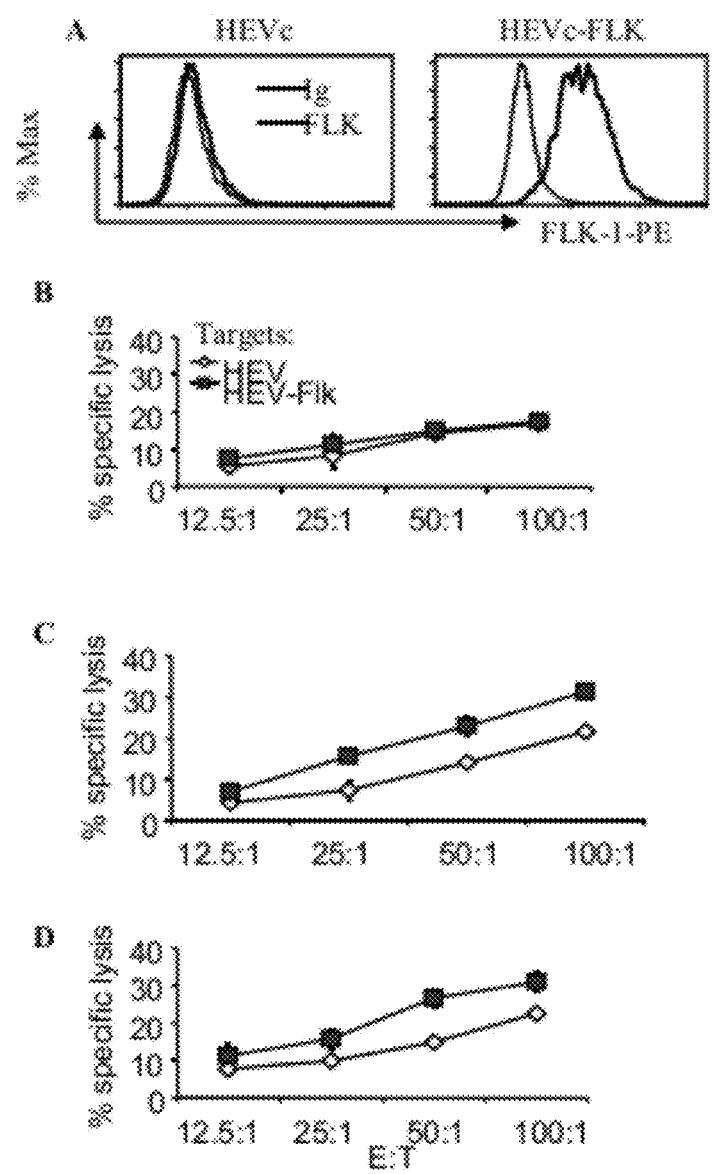
FIG. 15. (A) Surface expression of Flk-1 by the endothelial cell line HEVc and by HEVc cells stably transfected with Flk-1 (HEVc-Flk). Cells were washed and incubated with PE-conjugated isotype control Ab (thin grey lines), or PE-conjugated anti-Flk-1 Ab (thick black lines). Groups of immunized BALB/c mice (n=4) were sacrificed 2 weeks after the last immunization and splenocytes isolated from them were stimulated with irradiated HEVc-Flk cells for 5 days. Thereafter, cytotoxicity assays were performed with parental HEVc (a) or HEVc-Flk (■) as target cells. (B) Effector cells isolated from control group of mice immunized only with empty vector. (C) Effector cells from the pKd vaccinated group of mice. (D) Effector cells from the positive control group immunized with the Flk-1 whole gene vaccine.

Cytotoxicity assays were employed to demonstrate CTL activity of immunized mice. The target cells used were the murine endothelial cell line HEVc, and this same cell line stably transfected with Flk-1 plasmid (HEVc-Flk). Wild-type HEVc cells are Flk-, whereas HEVc-Flk cells readily express Flk-1 on the surface as indicated by flow cytometry analysis (FIG. 15, Panel A). Splenocytes isolated from empty vector control mice showed similar killing of HEVc-Flk cell as of HEVc parental cells (FIG. 15, Panel B). However, splenocytes from pKd-vaccinated mice induced significantly stronger killing against Flk$^+$ target cells (FIG. 15, Panel C). This killing capacity is very similar to that of splenocytes isolated from mice immunized with the whole Flk-1 gene vaccine (FIG. 15, Panel D). These data demonstrate the specificity of the pKd minigene vaccine-induced CTL activity and its capacity to kill Flk-1$^+$ proliferating endothelial cells.

The pKd minigene vaccine induced anti-angiogenesis effects. In an effort to investigate whether anti-angiogenesis played a key role in pKd-vaccine-induced tumor protection, tumor sections from immunized and control mice were analyzed by Masson's trichrome staining Tumor sections from empty vector control group mice showed ample, multiple blood vessels within the tumor mass. In contrast, blood vessels were rather scarce in tumor sections from pKd-vaccinated mice (FIG. 16, Panel A). These data demonstrate that immunization with the pKd vaccine resulted in the reduction of tumor vasculature.

Matrigel assays were also performed, in which blood vessel formation within the Matrigel was induced by recombinant bFGF. The difference in vessel formation was quantified by measuring the relative fluorescence intensity of extracts from Matrigel plugs obtained from immunized or control mice. Thus mice vaccinated with pKd vaccine displayed a reduction in average relative fluorescence (FIG. 16, Panel B). Taken together, these findings demonstrate that the pKd minigene vaccine induced marked anti-angiogenic effects, which aided in the protection of BALB/c mice from challenge with tumor cells of different origin in a prophylactic setting.

EXAMPLE 6

DNA Composition Encoding Immunogenic Fragments of a VEGF Receptor and Evaluation Therefor in a C57BL/6J Mouse Model Animals, bacterial strains, and cell lines. Male or female C57BL/6J mice were purchased from the Jackson Laboratory (Bar Harbor, Me.). All animal experiments were performed according to the National Institutes of Health Guides for the Care and Use of Laboratory Animals, and all protocols were approved by the Institutional Animal Care and Use Committee of The Scripps Research Institute.

The murine lung carcinoma cell line D121 was provided by Dr. L. Eisenbach (Weizmann Institute of Science, Rehovot, Israel). The murine prostate cancer cell line RM9 was obtained from Dr. T. C. Thompson (Baylor College of Medicine, Houston, Tex.). The murine breast cancer cell line EO771 was made available by Dr. D. Ross (University of Kentucky, Louisville, Ky.). Murine endothelial cell line, MS1, was purchased from the American Type Culture Collection (ATCC; Manassas, Va.). All cell lines were cultured in Dulbecco's modified Eagle medium (DMEM) (Invitrogen, Grand Island, N.Y.), supplemented with 10% (vol/vol) fetal bovine serum (FBS).

The double-attenuated S. typhimurium (AroA$^-$, dam$^-$) strain RE88 was provided by the Remedyne Corporation (Santa Barbara, Calif.), and was transformed with DNA vaccine plasmids as described above.

Figure 17:
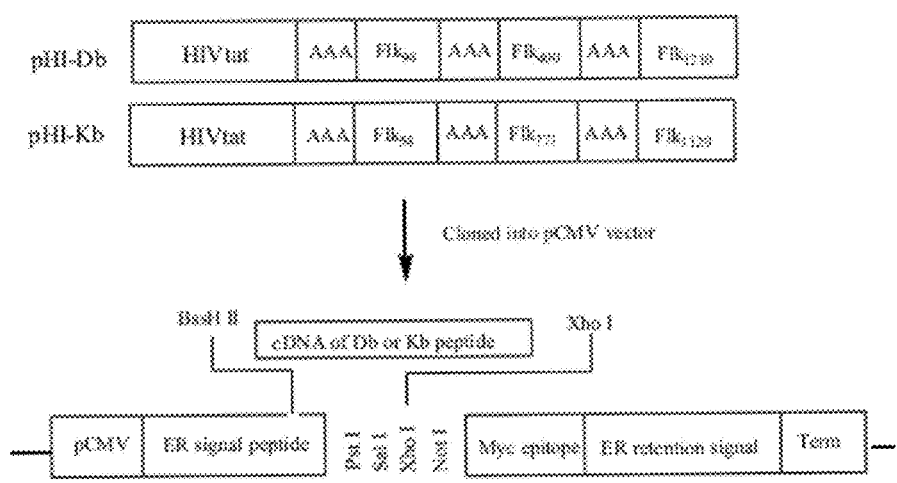
FIG. 17 illustrates minigenes encoding the murine pHI-Dd and pHI-Kb, which comprise immunogenic Flk-1 peptide fragments separated by AAA spacers, and including a HIVtat peptide at the N-terminus thereof. Vectors were assembled by PCR with overlapping oligonucleotides as templates as shown in the figure.

Construction of Expression Vectors. The expression vector pCMV/ER/Myc was purchased from Invitrogen (Carlsbad, Calif.). Vector construction is illustrated schematically in FIG. 17. The following expression vectors were constructed: pHI-myc, pHI-Db-myc, pHI-Kb-myc (See FIG. 17), where the HIVtat peptide (HI) represents RKKRRQRRR (SEQ ID NO: 17). The Flk$_{94}$, Flk$_{400}$, and Flk$_{1210}$ peptides stand for RVVGNDTGA (SEQ ID NO: 18), VILTNPISM (SEQ ID NO: 19), and FHYDNTAGI (SEQ ID NO: 20), respectively. Flk$_{54}$, Flk$_{771}$, and Flk$_{1129}$ peptides are designated for RGQRDLDWL (SEQ ID NO: 21), VIAMFFWLL (SEQ ID NO: 22), and TTPEMHYQTM (SEQ ID NO: 23), respectively. All peptides were engineered to be in-frame with the myc epitope. Constructs were confirmed by DNA sequencing at The Scripps Research Institute's Core Facility (La Jolla, Calif.). Peptide expression was demonstrated by Western blotting with monoclonal antibody (Invitrogen, Carlsbad, Calif.). Once peptide expression was verified, a stop codon was introduced immediately in front of the myc epitope sequences. The resulting vectors, namely pHI, pHI-Db, and pHI-Kb, were verified by nucleotide sequencing and use to transform double-attenuated S. typhimurium (dam-, AroA-) for immunization. The pCMV empty vector was also included in the experiments as a control.

Peptide Synthesis. All peptides were synthesized with more than 95% purity by high-performance liquid chromatography (HPLC) by Multiple Peptide Systems (San Diego, Calif.).

Oral Immunization and Tumor-Cell Challenge. Groups of C57BL/6J mice were immunized 3 times at 1-week intervals by gavage with 100 μL phosphate-buffered saline (PBS) containing approximately 5×10$^8$ double-attenuated RE88 S. typhimurium harboring either pCMV, pHI, pHI-Db, or pHI-Kb plasmids. Mice were challenged intravenously with different carcinoma cells 2 weeks after the last immunization.

Cytotoxicity and ELISPOT assays and in vivo depletion. Cytotoxicity was measured by a standard $^{51}$Cr-release assay as described above. The percentage of specific target cell lysis was calculated by the formula $[(E-S)/(T-S)] \times 100$, where E is the average experimental release, S the average spontaneous release, and T the average total release.

Enzyme-linked immunospot (ELISPOT) assays were performed with an ELISPOT kit (PharMingen, La Jolla, Calif.) according to the instructions provided by the manufacturer.

In vivo depletion was performed on vaccinated mice by intraperitoneal injection of anti-CD4 antibody (GK1.5, 0.4 mg/mouse) or anti-CD8 antibody (2.43, at 0.6 mg/mouse) 1 day before tumor challenge and repeated weekly.

Evaluation of Antiangiogenic Effects. Two weeks after the last vaccination, mice were given subcutaneous injections in the sternal region with 400 μL growth factor-reduced Matrigel (BD Biosciences, San Jose, Calif.) containing 400 ng/mL basic fibroblast growth factor (PeproTech, Rocky Hill, N.J.). In all mice, the endothelium was stained 6 days later by intravenous injection of 200 μL fluorescent Bandeiraea simplicifolia lectin I, isolectin B4 at 0.1 mg/mL (Vector Laboratories, Burlingame, Calif.). Fifteen minutes later, the Matrigel plugs were excised and evaluated by confocal microscopy (Axiovert 100TV microscope; Carl Zeiss, Oberkochem, Germany; 40×/1.3 NA objective; and SPOT camera and software), and then lectin-fluorescein isothiocyanate (FITC) was extracted with RIPA lysis buffer (0.15 mM NaCl/0.05 mM Tris [tris(hydroxymethyl)aminomethane]-HCl, pH 7.2/1% Triton X-100/1% sodium deoxycholate/0.1% sodium dodecyl sulfate) from 100-μg Matrigel plugs, to be quantified by fluorometry at 490 nm.

Statistical analysis. The statistical significance of differential findings between experimental groups and controls was determined by the Student t test. Findings were regarded as significant when 2-tailed P was less than 0.05.

Results

Minigenes encoded by expression vectors are expressed in mammalian cells. As demonstrated above, a DNA vaccine encoding the entire murine Flk-1 gene effectively induced $CD8^+$ T cell-mediated antiangiogenesis that protected mice from tumor-cell challenge. Here, a minigene approach was utilized to demonstrate that Flk-1 epitopes can induce similar antiangiogenic responses as the whole Flk-1 gene vaccine in a C57BL/6J mouse model. To this end, 3 peptides were included in $H-2D^b$- or $H-2K^b$-restricted minigenes based on the binding predicted for these MHC class 1 molecules using the HLA Peptide Binding Predictions program provided at the www website of the BioInformatics & Molecular Analysis Section (BIMAS) of the National Institutes of Health (NIH).

Expression vectors were constructed based on the backbone of pCMV/ER/Myc as described above. A HIVtat peptide (RKKRRQRRR, SEQ ID NO: 17), one of the commonly used membrane-translocating peptides, was also included in the minigene vaccine to facilitate the delivery of the encoded peptides. After transfection of 293 T cells with either pHI-myc, pHI-Dd-myc, or pHI-Kb-myc, correct expression of these constructs was demonstrated by Western blotting, which revealed single bands with the expected molecular mass of 15 kDa. The mature peptides did not contain the myc epitope because the vaccine vectors pHI, pHI-Db and pHI-Kb were generated by introducing a stop codon immediately downstream from the peptide-coding sequences. The correct vector constructs were confirmed by DNA sequencing. The empty pCMV vector was also included for control purposes.

The pHI-Db minigene vaccine protects mice against tumors of different origin by inducing immune responses that suppress tumor angiogenesis. Initially, the minigene DNA vaccines were evaluated in a prophylactic lung cancer model, where mice were first vaccinated with a minigene vaccine and then challenged intravenously with D121 lung carcinoma cells. In this case, the pHI-Db minigene elicited the best tumor protection, with 62.5% of mice surviving 75 days after tumor cell challenge. In contrast, none of the mice in the pCMV control group survived. The pHI or pHI-Kb vaccines induced only some tumor protection, however, with 25% of the mice surviving 75 days after tumor challenge.

To verify that the minigene vaccine effectively protects mice from tumors of different origins, the vaccine efficacy was also tested in a RM9 prostate carcinoma model. In this case, the pHI-Db minigene also protected the mice from RM9 tumor cell challenge indicating that the pHI-Db vaccine induces suppression of metastases independent of the tumor type.

In vivo depletion assays were performed to identify the cell population responsible for the tumor protection effects. Depletion of $CD8^+$ cells completely abrogated the vaccine-induced protection, whereas the depletion of $CD4^+$ cells moderately enhanced the protection against tumor challenge, indicating that the $CD8^+$ T cells are the major effectors.

The specificity of the CTL responses was further investigated in $^{51}$Cr-release assays. The pHI-Db vaccine induced a specific cytotoxic response against a Flk-1$^+$ endothelial cell line MS1, but not against Flk-1$^-$RM9 prostate carcinoma cells. These results indicate that the cytotoxic response induced by the pHI-Db vaccine was indeed directed against endothelial cells, presumably specific for Flk-1, rather than against tumor cells. This finding also provides evidence that the pHI-Db minigene vaccine would induce an antiangiogenic response in vivo.

Matrigel assays were also performed, which indicated that vaccination with minigene pHI-Db indeed suppressed vascularization. This was clearly demonstrated by reduced blood vessel formation observed in representative Matrigel plugs after in vivo staining of the endothelium with FITC-conjugated lectin. This difference in vessel formation was also demonstrated quantitatively by measuring the average relative fluorescence. Taken together, these findings demonstrate that the pHI-Db minigene vaccine induced antiangiogenic effects, which protected mice from challenge with tumor cells of different origin.

The pHI-Db Vaccine Induces a $Flk_{400}$-Specific Immune Response. To evaluate each of the 3 immunogenic Flk-1 peptide fragments encoded by the pHI-Db minigene, splenocytes isolated from mice immunized with pHI-Db were analyzed by ELISPOT assays using individual synthetic peptides as stimulators. A specific $Flk_{400}$ response was detected only in the pHI-Db-vaccinated group of mice, whereas no significant $Flk_{94}$- or $Flk_{1210}$-specific responses were found in any of the experimental groups of mice, suggesting that $Flk_{400}$ is the major epitope recognized by CTL effector cells.

To further confirm this observation, splenocytes from vaccinated mice were stimulated with synthetic peptides for 5 days and tested against MS1 and RM9 target cells in cytotoxicity assays. Only $Flk_{400}$-stimulated splenocytes exhibited specific cytotoxic killing against Flk-1$^+$MS1 target cells, but revealed almost no killing of Flk-1$^-$RM9 tumor cells. Splenocytes stimulated with $Flk_{94}$ induced low levels of MS1-specific killing whereas $Flk_{1210}$-stimulated splenocytes mainly displayed low levels of nonspecific killing, confirming the dominance of the $Flk_{400}$ epitope within the minigene vaccine.

When peptide-stimulated splenocytes isolated from pHI-Db-vaccinated mice were restimulated twice more in vitro with irradiated, peptide-loaded splenocytes every 7 days, and then tested again for their cytotoxicity, only those cells restimulated with $Flk_{400}$-loaded splenocytes showed greatly enhanced cytotoxicity, resulting in a higher percent specific killing at a much lower effector-target (E/T) ratio. In contrast, such restimulation with $Flk_{94}$-loaded splenocytes resulted in a lower level of MS1-specific killing, whereas cells restimulated with $Flk_{1210}$-loaded splenocytes failed to induce any significant killing. Taken together, these findings indicate that restimulation with $Flk_{400}$-loaded splenocytes enriches the CTL population that specifically targets Flk-1$^+$ endothelial cells.

The tumor protective ability of a minigene vaccine encoding only $Flk_{400}$ in the absence of $Flk_{94}$ and $Flk_{1210}$ was assessed and compared with the effect of the pHI-Db minigene vaccine in a EO771 breast carcinoma model. EO771 cells do not express Flk-1, but express surface $H-2D^b$ as detected by flow cytometry. In fact, both pHI-Db and pH1-$Flk_{400}$ minigene vaccines significantly protected the mice against EO771 tumor cell challenge to an extent comparable to the protection induced by the DNA vaccine of Example 1 encoding the entire Flk-1 gene. The pHI-Db vaccine also achieved similar efficacy as Flk-1 whole-gene vaccine in RM9 prostate and D121 lung carcinoma models.

Long-term protection was established by the pHI-Db minigene vaccine, as well. At 10 months after their last vaccination, pHI-Db-vaccinated mice showed significantly reduced lung metastases after intravenous challenging with EO771 breast carcinoma cells, an $Flk_{400}$-specific T cells could still be detected in the spleen of these mice.

The DNA Vaccine Encoding the Entire Elk-1 Gene Induces a $Flk_{400}$-specific CTL Response. The $Flk_{400}$-specific response was also induced by a DNA vaccine encoding the entire Flk-1 gene. Such responses were detected in splenocytes freshly isolated from pFlk-1-vaccinated mice as demonstrated by ELISPOT assays. These splenocytes maintained the specificity of the responses after in vitro stimulation with $Flk_{400}$ peptides. However, controls were negative, because stimulation with $Flk_{94}$ had no effect when compared to non-stimulated cells. Only nonspecific activation resulted from stimulation with $Flk_{1210}$. Moreover, splenocytes isolated from pFlk-1-vaccinated mice also displayed preferential cytotoxic killing of EO771 tumor cells loaded with $Flk_{400}$ as compared to the killing of unloaded EO771 cells. Similar results were also observed in pHI-Db-vaccinated mice, which were used as a positive control. The killing of EO771 or $Flk_{400}$-loaded EO771 tumor cells was largely indistinguishable in pCMV or pHI control groups. Taken together, these findings strongly indicate that the DNA vaccine encoding the entire Flk-1 gene was capable of inducing a $Flk_{400}$-specific immune response.

Numerous variations and modifications of the embodiments described above can be effected without departing from the spirit and scope of the novel features of the invention. It is to be understood that no limitations with respect to the specific embodiments illustrated herein are intended or should be inferred. It is, of course, intended to cover by the appended claims all such modifications as fall within the scope of the claims.

We claim:

1. A method of inhibiting endothelial cell proliferation in a mammal comprising the step of administering to the mammal an effective immunological response eliciting amount of a DNA composition comprising a DNA construct operably encoding a VEGF receptor polypeptide and a pharmaceutically acceptable carrier therefor, whereby said mammal exhibits an immune response elicited by vaccine and specific to proliferating endothelial cells, and wherein the DNA construct is operably incorporated in an attenuated bacterial vector.

2. The method of claim 1 wherein the mammal is a human.

3. The method of claim 1 wherein the VEGF receptor polypeptide is a full length protein selected from the group consisting of VEGFR-2 (KDR; SEQ ID NO: 2), VEGFR-1 (Flt-1; SEQ ID NO: 4), and Flk-1 (SEQ ID NO: 6).

4. The method of claim 1 wherein the attenuated bacterial vector is selected from attenuated *Salmonella typhimurium, Salmonella typhi, Shigella, Bacillus, Lactobacillus*, BCG, *Escherichia coli, Vibrio cholerae*, and *Campylobacter*.

5. The method of claim 4 wherein the attenuated bacterial vector is an attenuated *Salmonella typhimurium*.

6. The method of claim 1 wherein the composition is administered orally.

7. The method of claim 1 wherein the VEGF receptor polypeptide comprises at least one immunogenic VEGF receptor fragment consisting of about 8 to 10 consecutive amino acid residues of a VEGF receptor selected from the group consisting of VEGFR-2 (KDR; SEQ ID NO: 2), VEGFR-1 (Flt-1; SEQ ID NO: 4), and Flk-1 (SEQ ID NO: 6).

8. A method of inhibiting angiogenesis in a mammal comprising administering to said mammal an immunologically effective amount of a DNA composition comprising a DNA construct operably encoding a VEGF receptor polypeptide and a pharmaceutically acceptable carrier therefor, whereby said mammal exhibits an immune response elicited by vaccine and specific to proliferating endothelial cells, resulting in an inhibition of blood vessel formation, and wherein the DNA construct is operably incorporated in an attenuated bacterial vector.

9. The method of claim 8 wherein the mammal is a human.

10. The method of claim 8 wherein the VEGF receptor polypeptide is a full length VEGF receptor selected from the group consisting of VEGFR-2 (KDR; SEQ ID NO: 2), VEGFR-1 (Flt-1; SEQ ID NO: 4), and Flk-1 (SEQ ID NO: 6).

11. The method of claim 8 wherein the VEGF receptor polypeptide comprises at least one immunogenic VEGF receptor fragment consisting of about 8 to 10 consecutive amino acid residues of a VEGF receptor selected from the group consisting of VEGFR-2 (KDR; SEQ ID NO: 2), VEGFR-1 (Flt-1; SEQ ID NO: 4), and Flk-1 (SEQ ID NO: 6).

12. The method of claim 8 wherein the attenuated bacterial vector is selected from attenuated *Salmonella typhimurium, Salmonella typhi, Shigella, Bacillus, Lactobacillus*, BCG, *Escherichia coli, Vibrio cholerae*, and *Campylobacter*.

13. The method of claim 8 wherein the attenuated bacterial vector is an attenuated *Salmonella typhimurium*.

14. The method of claim 8 wherein the vaccine is administered orally.

15. A method of inhibiting tumor growth in a mammal comprising administering to said mammal an immunologically effective amount of a DNA composition comprising a DNA construct operably encoding a VEGF receptor polypeptide and a pharmaceutically acceptable carrier therefor, whereby said mammal exhibits an immune response elicited by vaccine and specific to proliferating endothelial cells, resulting in the arresting of tumor growth, reduction in tumor size, or inhibition of tumor dissemination and wherein the DNA construct is operably incorporated in an attenuated bacterial vector.

16. The method of claim 15 wherein the mammal is a human.

17. The method of claim 15 wherein the VEGF receptor polypeptide is a full length VEGF receptor selected from the group consisting of VEGFR-2 (KDR; SEQ ID NO: 2), VEGFR-1 (Flt-1; SEQ ID NO: 4), and Flk-1 (SEQ ID NO: 6).

18. The method of claim 15 wherein the VEGF receptor polypeptide comprises at least one immunogenic VEGF receptor fragment consisting of about 8 to 10 consecutive amino acid residues of a VEGF receptor selected from the group consisting of VEGFR-2 (KDR; SEQ ID NO: 2), VEGFR-1 (Flt-1; SEQ ID NO: 4), and Flk-1 (SEQ ID NO: 6).

19. The method of claim 15 wherein the attenuated bacterial vector is selected from attenuated *Salmonella typhimurium, Salmonella typhi, Shigella, Bacillus, Lactobacillus*, BCG, *Escherichia coli, Vibrio cholerae*, and *Campylobacter.*

20. The method of claim 15 wherein the attenuated bacterial vector is an attenuated *Salmonella typhimurium*.

21. The method of claim 15 wherein the vaccine is administered orally.

22. The method of claim 15 wherein the attenuated bacterial vector is an attenuated *Salmonella typhi*.

23. The method of claim 1 wherein the attenuated bacterial vector is an attenuated *Salmonella typhi*.

24. The method of claim 8 wherein the attenuated bacterial vector is an attenuated *Salmonella typhi*.

* * * * *

```
                            SEQUENCE LISTING

<160> NUMBER OF SEQ ID NOS: 23

<210> SEQ ID NO 1
<211> LENGTH: 4071
<212> TYPE: DNA
<213> ORGANISM: human

<400> SEQUENCE: 1
atggagagca aggtgctgct ggccgtcgcc ctgtggctct gcgtggagac ccggccgcc       60 tctgtgggtt tgcctagtgt ttctcttgat ctgcccaggc tcagcataca aaaagacata     120
cttacaatta aggctaatac aactcttcaa attacttgca ggggacagag ggacttggac     180
tggctttggc ccaataatca gagtggcagt gagcaaaggt ggaggtgac tgagtgcagc      240 gatggcctct tctgtaagac actcacaatt ccaaaagtga tcggaaatga cactggagcc     300
tacaagtgct tctaccggga aactgacttg gcctcggtca tttatgtcta tgttcaagat     360
tacagatctc catttattgc ttctgttagt gaccaacatg gagtcgtgta cattactgag     420
aacaaaaaca aaactgtggt gattccatgt ctcgggtcca tttcaaatct caacgtgtca     480
ctttgtgcaa gatacccaga aaagagattt gttcctgatg gtaacagaat tcctgggac     540 agcaagaagg gctttactat tcccagctac atgatcagct atgctggcat ggtcttctgt     600
gaagcaaaaa ttaatgatga agttaccag tctattatgt acatagttgt cgttgtaggg      660
tataggattt atgatgtggt tctgagtccg tctcatggaa ttgaactatc tgttggagaa     720
aagcttgtct taaattgtac agcaagaact gaactaaatg tggggattga cttcaactgg     780
gaataccctt cttcgaagca tcagcataag aaacttgtaa accgagacct aaaaaccccag    840 tctgggagtg agatgaagaa atttttgagc accttaacta tagatggtgt aacccggagt     900
gaccaaggat tgtacacctg tgcagcatcc agtgggctga tgaccaagaa gaacagcaca     960
tttgtcaggg tccatgaaaa acctttttgtt gcttttggaa gtggcatgga atctctggtg    1020 gaagccacg tggggagcg tgtcagaatc cctgcgaagt accttggtta cccacccca       1080 gaaataaaat ggtataaaaa tggaatacc cttgagtcca atcacacaat taaagcgggg      1140
catgtactga cgattatgga agtgagtgaa agagacacag gaaattacac tgtcatcctt     1200
accaatccca tttcaaagga gaagcagagc catgtggtct ctctggttgt gtatgtccca    1260
ccccagattg tgagaaatc tctaatctct cctgtggatt cctaccagta cggcaccact      1320
caaacgctga catgtacggt ctatgccatt cctccccgc atcacatcca ctggtattgg      1380
cagttggagg aagagtgcgc caacgagccc agccaagctg tctcagtgac aaacccatac    1440
ccttgtgaag aatggagaag tgtggaggac ttccagggag gaaataaaat tgaagttaat    1500
aaaaatcaat ttgctctaat tgaaggaaaa aacaaaactg taagtaccct tgttatccaa    1560
```

```
gcggcaaatg tgtcagcttt gtacaaatgt gaagcggtca acaaagtcgg gagaggagag   1620
agggtgatct ccttccacgt gaccaggggt cctgaaatta ctttgcaacc tgacatgcag   1680
cccactgagc aggagagcgt gtctttgtgg tgcactgcag acagatctac gtttgagaac   1740
ctcacatggt acaagcttgg cccacagcct ctgccaatcc atgtgggaga gttgcccaca   1800 cctgttttgca agaacttgga tactctttgg aaattgaatg ccaccatgtt ctctaatagc   1860
acaaatgaca ttttgatcat ggagcttaag aatgcatcct tgcaggacca aggagactat   1920
gtctgccttg ctcaagacag gaagaccaag aaaagacatt gcgtggtcag gcagctcaca   1980
gtcctagagc gtgtggcacc cacgatcaca ggaaacctgg agaatcagac gacaagtatt   2040
ggggaaagca tcgaagtctc atgcacggca tctgggaatc cccctccaca gatcatgtgg   2100
tttaaagata atgagaccct tgtagaagac tcaggcattg tattgaagga tgggaaccgg   2160
aacctcacta tccgcagagt gaggaaggag gacgaaggcc tctacacctg ccaggcatgc   2220
agtgttcttg gctgtgcaaa agtggaggca ttttttcataa tagaaggtgc ccaggaaaag   2280
acgaacttgg aaatcattat tctagtaggc acggcggtga ttgccatgtt cttctggcta   2340
cttcttgtca tcatcctacg gaccgttaag cgggccaatg gaggggaact gaagacaggc   2400
tacttgtcca tcgtcatgga tccagatgaa ctcccattgg atgaacattg tgaacgactg   2460
ccttatgatg ccagcaaatg ggaattcccc agagaccggc tgaagctagg taagcctctt   2520
ggccgtggtg cctttggcca agtgattgaa gcagatgcct ttggaattga caagacagca   2580
acttgcagga cagtagcagt caaaatgttg aagaaggag caacacacag tgagcatcga   2640
gctctcatgt ctgaactcaa gatcctcatt catattggtc accatctcaa tgtggtcaac   2700
cttctaggtg cctgtaccaa gccaggaggg ccactcatgg tgattgtgga attctgcaaa   2760
tttggaaacc tgtccactta cctgaggagc aagagaaatg aatttgtccc ctacaagacc   2820 aaagggcac gattccgtca agggaaagac tacgttggag caatccctgt ggatctgaaa   2880
cggcgcttgg acagcatcac cagtagccag agctcagcca gctctggatt tgtggaggag   2940
aagtccctca gtgatgtaga agaagaggaa gctcctgaag atctgtataa ggacttcctg   3000
accttggagc atctcatctg ttacagcttc caagtggcta agggcatgga gttcttggca   3060
tcgcgaaagt gtatccacag ggaccttgcg gcacgaaata tcctcttatc ggagaagaac   3120
gtggttaaaa tctgtgactt tggcttggcc cgggatattt ataaagatcc agattatgtc   3180
agaaaaggag atgctcgcct ccctttgaaa tggatggccc cagaaacaat ttttgacaga   3240
gtgtacacaa tccagagtga cgtctggtct tttggtgttt tgctgtggga aatattttcc   3300
ttaggtgctt ctccatatcc tggggtaaag attgatgaag aattttgtag gcgattgaaa   3360
gaaggaacta gaatgagggc ccctgattat actacaccag aaaatgtacca gaccatgctg   3420 gactgctggc acgggagcc cagtcagaga cccacgtttt cagagttggt ggaacatttg   3480
ggaaatctct tgcaagctaa tgctcagcag gatggcaaag actacattgt tcttccgata   3540
tcagagactt tgagcatgga agaggattct ggactctctc tgcctacctc acctgttttcc   3600 tgtatggagg aggaggaagt atgtgacccc aaattccatt atgacaacac agcaggaatc   3660
agtcagtatc tgcagaacag taagcgaaag agccggcctg tgagtgtaaa aacatttgaa   3720
gatatcccgt tagaagaacc agaagtaaaa gtaatcccag atgacaacca gacggacagt   3780
ggtatggttc ttgcctcaga agagctgaaa actttggaag acagaaccaa attatctcca   3840
tcttttggtg aatggtgcc cagcaaaagc agggagtctg tggcatctga aggctcaaac   3900
cagacaagcg gctaccagtc cggatatcac tccgatgaca cagacaccac cgtgtactcc   3960
```

```
agtgaggaag cagaactttt aaagctgata gagattggag tgcaaaccgg tagcacagcc      4020
cagattctcc agcctgactc ggggaccaca ctgagctctc tcctgttta a                4071
```

<210> SEQ ID NO 2
<211> LENGTH: 1356
<212> TYPE: PRT
<213> ORGANISM: human

<400> SEQUENCE: 2

```
Met Gln Ser Lys Val Leu Leu Ala Val Ala Leu Trp Leu Cys Val Glu
 1               5                  10                  15

Thr Arg Ala Ala Ser Val Gly Leu Pro Ser Val Ser Leu Asp Leu Pro
                20                  25                  30

Arg Leu Ser Ile Gln Lys Asp Ile Leu Thr Ile Lys Ala Asn Thr Thr
            35                  40                  45

Leu Gln Ile Thr Cys Arg Gly Gln Arg Asp Leu Asp Trp Leu Trp Pro
        50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
```

```
                355                 360                 365
Ile Pro Leu Glu Ser Asn His Thr Ile Lys Ala Gly His Val Leu Thr
370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
                420                 425                 430

Asp Ser Tyr Gln Tyr Gly Thr Thr Gln Thr Leu Thr Cys Thr Val Tyr
            435                 440                 445

Ala Ile Pro Pro Pro His His Ile His Trp Tyr Trp Gln Leu Glu Glu
        450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
                500                 505                 510

Thr Val Ser Thr Leu Val Ile Gln Ala Ala Asn Val Ser Ala Leu Tyr
            515                 520                 525

Lys Cys Glu Ala Val Asn Lys Val Gly Arg Gly Glu Arg Val Ile Ser
530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
                580                 585                 590

Ile His Val Gly Glu Leu Pro Thr Pro Val Cys Lys Asn Leu Asp Thr
            595                 600                 605

Leu Trp Lys Leu Asn Ala Thr Met Phe Ser Asn Ser Thr Asn Asp Ile
610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Arg His Cys Val Val
                645                 650                 655

Arg Gln Leu Thr Val Leu Glu Arg Val Ala Pro Thr Ile Thr Gly Asn
                660                 665                 670

Leu Glu Asn Gln Thr Thr Ser Ile Gly Glu Ser Ile Glu Val Ser Cys
            675                 680                 685

Thr Ala Ser Gly Asn Pro Pro Pro Gln Ile Met Trp Phe Lys Asp Asn
        690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
                740                 745                 750

Ile Ile Glu Gly Ala Gln Glu Lys Thr Asn Leu Glu Ile Ile Ile Leu
            755                 760                 765

Val Gly Thr Ala Val Ile Ala Met Phe Phe Trp Leu Leu Leu Val Ile
770                 775                 780
```

-continued

```
Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
            805                 810                 815

Cys Glu Arg Leu Pro Tyr Asp Ala Ser Lys Trp Glu Phe Pro Arg Asp
        820                 825                 830

Arg Leu Lys Leu Gly Lys Pro Leu Gly Arg Gly Ala Phe Gly Gln Val
    835                 840                 845

Ile Glu Ala Asp Ala Phe Gly Ile Asp Lys Thr Ala Thr Cys Arg Thr
850                 855                 860

Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
                885                 890                 895

Asn Val Val Asn Leu Leu Gly Ala Cys Thr Lys Pro Gly Gly Pro Leu
            900                 905                 910

Met Val Ile Val Glu Phe Cys Lys Phe Gly Asn Leu Ser Thr Tyr Leu
        915                 920                 925

Arg Ser Lys Arg Asn Glu Phe Val Pro Tyr Lys Thr Lys Gly Ala Arg
    930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
                965                 970                 975

Phe Val Glu Glu Lys Ser Leu Ser Asp Val Glu Glu Glu Glu Ala Pro
            980                 985                 990

Glu Asp Leu Tyr Lys Asp Phe Leu Thr Leu Glu His Leu Ile Cys Tyr
        995                 1000                1005

Ser Phe Gln Val Ala Lys Gly Met Glu Phe Leu Ala Ser Arg Lys Cys
    1010                1015                1020

Ile His Arg Asp Leu Ala Ala Arg Asn Ile Leu Leu Ser Glu Lys Asn
1025                1030                1035                1040

Val Val Lys Ile Cys Asp Phe Gly Leu Ala Arg Asp Ile Tyr Lys Asp
                1045                1050                1055

Pro Asp Tyr Val Arg Lys Gly Asp Ala Arg Leu Pro Leu Lys Trp Met
            1060                1065                1070

Ala Pro Glu Thr Ile Phe Asp Arg Val Tyr Thr Ile Gln Ser Asp Val
        1075                1080                1085

Trp Ser Phe Gly Val Leu Leu Trp Glu Ile Phe Ser Leu Gly Ala Ser
    1090                1095                1100

Pro Tyr Pro Gly Val Lys Ile Asp Glu Glu Phe Cys Arg Arg Leu Lys
1105                1110                1115                1120

Glu Gly Thr Arg Met Arg Ala Pro Asp Tyr Thr Thr Pro Glu Met Tyr
                1125                1130                1135

Gln Thr Met Leu Asp Cys Trp His Gly Glu Pro Ser Gln Arg Pro Thr
            1140                1145                1150

Phe Ser Glu Leu Val Glu His Leu Gly Asn Leu Leu Gln Ala Asn Ala
        1155                1160                1165

Gln Gln Asp Gly Lys Asp Tyr Ile Val Leu Pro Ile Ser Glu Thr Leu
    1170                1175                1180

Ser Met Glu Glu Asp Ser Gly Leu Ser Leu Pro Thr Ser Pro Val Ser
1185                1190                1195                1200

Cys Met Glu Glu Glu Glu Val Cys Asp Pro Lys Phe His Tyr Asp Asn
                1205                1210                1215
```

Thr Ala Gly Ile Ser Gln Tyr Leu Gln Asn Ser Lys Arg Lys Ser Arg
        1220                1225                1230

Pro Val Ser Val Lys Thr Phe Glu Asp Ile Pro Leu Glu Glu Pro Glu
    1235                1240                1245

Val Lys Val Ile Pro Asp Asp Asn Gln Thr Asp Ser Gly Met Val Leu
    1250                1255                1260

Ala Ser Glu Glu Leu Lys Thr Leu Glu Asp Arg Thr Lys Leu Ser Pro
1265                1270                1275                1280

Ser Phe Gly Gly Met Val Pro Ser Lys Ser Arg Glu Ser Val Ala Ser
                1285                1290                1295

Glu Gly Ser Asn Gln Thr Ser Gly Tyr Gln Ser Gly Tyr His Ser Asp
            1300                1305                1310

Asp Thr Asp Thr Thr Val Tyr Ser Ser Glu Glu Ala Glu Leu Leu Lys
        1315                1320                1325

Leu Ile Glu Ile Gly Val Gln Thr Gly Ser Thr Ala Gln Ile Leu Gln
    1330                1335                1340

Pro Asp Ser Gly Thr Thr Leu Ser Ser Pro Pro Val
1345                1350                1355

<210> SEQ ID NO 3
<211> LENGTH: 4017
<212> TYPE: DNA
<213> ORGANISM: human

<400> SEQUENCE: 3
atggtcagct actgggacac cggggtcctg ctgtgcgcgc tgctcagctg tctgcttctc       60
acaggatcta gttcaggttc aaaattaaaa gatcctgaac tgagtttaaa aggcacccag      120
cacatcatgc aagcaggcca gacactgcat ctccaatgca gggggaagc agcccataaa      180 tggtctttgc ctgaaatggt gagtaaggaa agcgaaaggc tgagcataac taaatctgcc      240
tgtggaagaa atggcaaaca attctgcagt actttaacct tgaacacagc tcaagcaaac      300
cacactggct tctacagctg caaatatcta gctgtaccta cttcaaagaa gaaggaaaca      360
gaatctgcaa tctatatatt tattagtgat acaggtagcc ttttcgtaga gatgtacagt      420
gaaatccccg aaattataca catgactgaa ggaagggagc tcgtcattcc ctgccgggtt      480
acgtcaccta catcactgt tactttaaaa agtttccac ttgacacttt gatccctgat      540
ggaaaacgca atctgggga cagtagaaag ggcttcatca tatcaaatgc aacgtacaaa      600
gaaatagggc ttctgacctg tgaagcaaca gtcaatgggc atttgtataa gacaaactat      660
ctcacacatc gacaaaccaa tacaatcata gatgtccaaa taagcacacc acgcccagtc      720
aaattactta aggccataca tcttgtcctc aattgtactg ctaccactcc cttgaacacg      780
agagttcaaa tgacctggag ttaccctgat gaaaaaaata gagagcttc cgtaaggcga      840 cgaattgacc aaagcaattc ccatgccaac atattctaca gtgttcttac tattgacaaa      900
atgcagaaca agacaaagg actttatact tgtcgtgtaa ggagtggacc atcattcaaa      960
tctgttaaca cctcagtgca tatatatgat aaagcattca tcactgtgaa acatcgaaaa     1020
cagcaggtgc ttgaaaccgt agctggcaag cggtcttacc ggctctctat gaaagtgaag     1080
gcatttccct cgccggaagt tgtatggtta aaagatgggt acctgcgac tgagaaatct     1140 gctcgctatt tgactcgtgg ctactcgtta attatcaagg acgtaactga agaggatgca     1200
gggaattata caatcttgct gagcataaaa cagtcaaatg tgtttaaaaa cctcactgcc     1260
actctaattg tcaatgtgaa acccagatt tacgaaaagg ccgtgtcatc gtttccagac     1320

```
ccggctctct acccactggg cagcagacaa atcctgactt gtaccgcata tggtatccct    1380
caacctacaa tcaagtggtt ctggcacccc tgtaaccata atcattccga agcaaggtgt    1440
gacttttgtt ccaataatga agagtccttt atcctggatg ctgacagcaa catgggaaac    1500
agaattgaga gcatcactca gcgcatggca ataatagaag gaaagaataa gatggctagc    1560
accttggttg tggctgactc tagaatttct ggaatctaca tttgcatagc ttccaataaa    1620
gttgggactg tgggaagaaa cataagcttt tatatcacag atgtgccaaa tgggtttcat    1680
gttaacttgg aaaaaatgcc gacggaagga gaggacctga aactgtcttg cacagttaac    1740
aagttcttat acagagacgt tacttggatt ttactgcgga cagttaataa cagaacaatg    1800
cactacagta ttagcaagca aaaaatggcc atcactaagg agcactccat cactcttaat    1860
cttaccatca tgaatgtttc cctgcaagat tcaggcacct atgcctgcag agccaggaat    1920
gtatacacag gggaagaaat cctccagaag aaagaaatta caatcagaga tcaggaagca    1980
ccatacctcc tgcgaaacct cagtgatcac acagtggcca tcagcagttc caccactta    2040 gactgtcatg ctaatggtgt ccccgagcct cagatcactt ggtttaaaaa caaccacaaa    2100
atacaacaag agcctggaat tattttagga ccaggaagca gcacgctgtt tattgaaaga    2160
gtcacagaag aggatgaagg tgtctatcac tgcaaagcca ccaaccagaa gggctctgtg    2220
gaaagttcag catacctcac tgttcaagga acctcggaca agtctaatct ggagctgatc    2280
actctaacat gcacctgtgt ggctgcgact ctcttctggc tcctattaac cctctttatc    2340
cgaaaaatga aaaggtcttc ttctgaaata aagactgact acctatcaat tataatggac    2400
ccagatgaag ttcctttgga tgagcagtgt gagcggctcc cttatgatgc cagcaagtgg    2460
gagtttgccc gggagagact aaaactgggc aaatcacttg aagaggggc ttttggaaaa    2520 gtggttcaag catcagcatt tggcattaag aaatcaccta cgtgccggac tgtggctgtg    2580
aaaatgctga agagggggc cacggccagc gagtacaaag ctctgatgac tgagctaaaa    2640
atcttgaccc acattggcca ccatctgaac gtggttaacc tgctgggagc ctgcaccaag    2700
caaggagggc ctctgatggt gattgttgaa tactgcaaat atggaaatct ctccaactac    2760
ctcaagagca aacgtgactt attttttctc aacaaggatg cagcactaca catggagcct    2820
aagaaagaaa aaatggagcc aggcctggaa caaggcaaga accaagact agatagcgtc    2880 accagcagcg aaagctttgc gagctccggc tttcaggaag ataaagtct gagtgatgtt    2940 gaggaagagg aggattctga cggtttctac aaggagccca tcactatgga agatctgatt    3000
tcttacagtt ttcaagtggc cagaggcatg gagttcctgt cttccagaaa gtgcattcat    3060
cgggacctgg cagcgagaaa cattcttta tctgagaaca cgtggtgaa gatttgtgat    3120 tttggccttg cccgggatat ttataagaac cccgattatg tgagaaaagg agatactcga    3180
cttcctctga aatggatggc tcctgaatct atctttgaca aaatctacag caccaagagc    3240
gacgtgtggg cttacggagt attgctgtgg gaaatcttct ccttaggtgg gtctccatac    3300
ccaggagtac aaatggatga ggacttttgc agtcgcctga gggaaggcat gaggatgaga    3360
gctcctgagt actctactcc tgaaatctat cagatcatgc tggactgctg gcacagagac    3420
ccaaaagaaa ggccaagatt tgcagaactt gtggaaaaac taggtgattt gcttcaagca    3480
aatgtacaac aggatggtaa agactacatc ccaatcaatg ccatactgac aggaaatagt    3540
gggtttacat actcaactcc tgccttctct gaggacttct tcaaggaaag tatttcagct    3600 ccgaagtttta attcaggaag ctctgatgat gtcagatatg taaatgcttt caagttcatg    3660
agcctggaaa gaatcaaaac cttttgaagaa cttttaccga atgccacctc catgtttgat    3720
```

```
gactaccagg gcgacagcag cactctgttg gcctctccca tgctgaagcg cttcacctgg   3780
actgacagca aacccaaggc ctcgctcaag attgacttga gagtaaccag taaaagtaag   3840
gagtcggggc tgtctgatgt cagcaggccc agtttctgcc attccagctg tgggcacgtc   3900
agcgaaggca agcgcaggtt cacctacgac cacgctgagc tggaaaggaa aatcgcgtgc   3960
tgctccccgc ccccagacta caactcggtg gtcctgtact ccaccccacc catctag     4017
```

<210> SEQ ID NO 4
<211> LENGTH: 1338
<212> TYPE: PRT
<213> ORGANISM: human

<400> SEQUENCE: 4

```
Met Val Ser Tyr Trp Asp Thr Gly Val Leu Leu Cys Ala Leu Leu Ser
 1               5                  10                  15

Cys Leu Leu Leu Thr Gly Ser Ser Ser Gly Ser Lys Leu Lys Asp Pro
             20                  25                  30

Glu Leu Ser Leu Lys Gly Thr Gln His Ile Met Gln Ala Gly Gln Thr
         35                  40                  45

Leu His Leu Gln Cys Arg Gly Glu Ala Ala His Lys Trp Ser Leu Pro
     50                  55                  60

Glu Met Val Ser Lys Glu Ser Glu Arg Leu Ser Ile Thr Lys Ser Ala
 65                  70                  75                  80

Cys Gly Arg Asn Gly Lys Gln Phe Cys Ser Thr Leu Thr Leu Asn Thr
                 85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335
```

-continued

```
Lys His Arg Lys Gln Gln Val Leu Glu Thr Val Ala Gly Lys Arg Ser
            340                 345                 350
Tyr Arg Leu Ser Met Lys Val Lys Ala Phe Pro Ser Pro Glu Val Val
            355                 360                 365
Trp Leu Lys Asp Gly Leu Pro Ala Thr Glu Lys Ser Ala Arg Tyr Leu
    370                 375                 380
Thr Arg Gly Tyr Ser Leu Ile Ile Lys Asp Val Thr Glu Glu Asp Ala
385                 390                 395                 400
Gly Asn Tyr Thr Ile Leu Leu Ser Ile Lys Gln Ser Asn Val Phe Lys
                405                 410                 415
Asn Leu Thr Ala Thr Leu Ile Val Asn Val Lys Pro Gln Ile Tyr Glu
                420                 425                 430
Lys Ala Val Ser Ser Phe Pro Asp Pro Ala Leu Tyr Pro Leu Gly Ser
            435                 440                 445
Arg Gln Ile Leu Thr Cys Thr Ala Tyr Gly Ile Pro Gln Pro Thr Ile
450                 455                 460
Lys Trp Phe Trp His Pro Cys Asn His Asn His Ser Glu Ala Arg Cys
465                 470                 475                 480
Asp Phe Cys Ser Asn Asn Glu Glu Ser Phe Ile Leu Asp Ala Asp Ser
                485                 490                 495
Asn Met Gly Asn Arg Ile Glu Ser Ile Thr Gln Arg Met Ala Ile Ile
                500                 505                 510
Glu Gly Lys Asn Lys Met Ala Ser Thr Leu Val Val Ala Asp Ser Arg
            515                 520                 525
Ile Ser Gly Ile Tyr Ile Cys Ile Ala Ser Asn Lys Val Gly Thr Val
            530                 535                 540
Gly Arg Asn Ile Ser Phe Tyr Ile Thr Asp Val Pro Asn Gly Phe His
545                 550                 555                 560
Val Asn Leu Glu Lys Met Pro Thr Glu Gly Glu Asp Leu Lys Leu Ser
                565                 570                 575
Cys Thr Val Asn Lys Phe Leu Tyr Arg Asp Val Thr Trp Ile Leu Leu
            580                 585                 590
Arg Thr Val Asn Asn Arg Thr Met His Tyr Ser Ile Ser Lys Gln Lys
            595                 600                 605
Met Ala Ile Thr Lys Glu His Ser Ile Thr Leu Asn Leu Thr Ile Met
    610                 615                 620
Asn Val Ser Leu Gln Asp Ser Gly Thr Tyr Ala Cys Arg Ala Arg Asn
625                 630                 635                 640
Val Tyr Thr Gly Glu Glu Ile Leu Gln Lys Lys Glu Ile Thr Ile Arg
                645                 650                 655
Asp Gln Glu Ala Pro Tyr Leu Leu Arg Asn Leu Ser Asp His Thr Val
            660                 665                 670
Ala Ile Ser Ser Ser Thr Thr Leu Asp Cys His Ala Asn Gly Val Pro
            675                 680                 685
Glu Pro Gln Ile Thr Trp Phe Lys Asn Asn His Lys Ile Gln Gln Glu
    690                 695                 700
Pro Gly Ile Ile Leu Gly Pro Gly Ser Ser Thr Leu Phe Ile Glu Arg
705                 710                 715                 720
Val Thr Glu Glu Asp Glu Gly Val Tyr His Cys Lys Ala Thr Asn Gln
                725                 730                 735
Lys Gly Ser Val Glu Ser Ser Ala Tyr Leu Thr Val Gln Gly Thr Ser
            740                 745                 750
Asp Lys Ser Asn Leu Glu Leu Ile Thr Leu Thr Cys Thr Cys Val Ala
```

```
              755                 760                 765
Ala Thr Leu Phe Trp Leu Leu Leu Thr Leu Phe Ile Arg Lys Met Lys
770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
                805                 810                 815

Ala Ser Lys Trp Glu Phe Ala Arg Glu Arg Leu Lys Leu Gly Lys Ser
            820                 825                 830

Leu Gly Arg Gly Ala Phe Gly Lys Val Val Gln Ala Ser Ala Phe Gly
        835                 840                 845

Ile Lys Lys Ser Pro Thr Cys Arg Thr Val Ala Val Lys Met Leu Lys
    850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
                885                 890                 895

Ala Cys Thr Lys Gln Gly Gly Pro Leu Met Val Ile Val Glu Tyr Cys
            900                 905                 910

Lys Tyr Gly Asn Leu Ser Asn Tyr Leu Lys Ser Lys Arg Asp Leu Phe
        915                 920                 925

Phe Leu Asn Lys Asp Ala Ala Leu His Met Glu Pro Lys Lys Glu Lys
    930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
                965                 970                 975

Leu Ser Asp Val Glu Glu Glu Asp Ser Asp Gly Phe Tyr Lys Glu
            980                 985                 990

Pro Ile Thr Met Glu Asp Leu Ile Ser Tyr Ser Phe Gln Val Ala Arg
        995                 1000                1005

Gly Met Glu Phe Leu Ser Ser Arg Lys Cys Ile His Arg Asp Leu Ala
    1010                1015                1020

Ala Arg Asn Ile Leu Leu Ser Glu Asn Asn Val Val Lys Ile Cys Asp
1025                1030                1035                1040

Phe Gly Leu Ala Arg Asp Ile Tyr Lys Asn Pro Asp Tyr Val Arg Lys
                1045                1050                1055

Gly Asp Thr Arg Leu Pro Leu Lys Trp Met Ala Pro Glu Ser Ile Phe
            1060                1065                1070

Asp Lys Ile Tyr Ser Thr Lys Ser Asp Val Trp Ser Tyr Gly Val Leu
        1075                1080                1085

Leu Trp Glu Ile Phe Ser Leu Gly Gly Ser Pro Tyr Pro Gly Val Gln
    1090                1095                1100

Met Asp Glu Asp Phe Cys Ser Arg Leu Arg Glu Gly Met Arg Met Arg
1105                1110                1115                1120

Ala Pro Glu Tyr Ser Thr Pro Glu Ile Tyr Gln Ile Met Leu Asp Cys
                1125                1130                1135

Trp His Arg Asp Pro Lys Glu Arg Pro Arg Phe Ala Glu Leu Val Glu
            1140                1145                1150

Lys Leu Gly Asp Leu Leu Gln Ala Asn Val Gln Gln Asp Gly Lys Asp
        1155                1160                1165

Tyr Ile Pro Ile Asn Ala Ile Leu Thr Gly Asn Ser Gly Phe Thr Tyr
    1170                1175                1180
```

```
Ser Thr Pro Ala Phe Ser Glu Asp Phe Phe Lys Glu Ser Ile Ser Ala
1185                1190                1195                1200

Pro Lys Phe Asn Ser Gly Ser Asp Asp Val Arg Tyr Val Asn Ala
            1205                1210                1215

Phe Lys Phe Met Ser Leu Glu Arg Ile Lys Thr Phe Glu Glu Leu Leu
        1220                1225                1230

Pro Asn Ala Thr Ser Met Phe Asp Asp Tyr Gln Gly Asp Ser Ser Thr
            1235                1240                1245

Leu Leu Ala Ser Pro Met Leu Lys Arg Phe Thr Trp Thr Asp Ser Lys
        1250                1255                1260

Pro Lys Ala Ser Leu Lys Ile Asp Leu Arg Val Thr Ser Lys Ser Lys
1265                1270                1275                1280

Glu Ser Gly Leu Ser Asp Val Ser Arg Pro Ser Phe Cys His Ser Ser
                1285                1290                1295

Cys Gly His Val Ser Glu Gly Lys Arg Arg Phe Thr Tyr Asp His Ala
            1300                1305                1310

Glu Leu Glu Arg Lys Ile Ala Cys Cys Ser Pro Pro Asp Tyr Asn
        1315                1320                1325

Ser Val Val Leu Tyr Ser Thr Pro Pro Ile
        1330                1335

<210> SEQ ID NO 5
<211> LENGTH: 5390
<212> TYPE: DNA
<213> ORGANISM: mouse

<400> SEQUENCE: 5
ctgtgtcccg cagccggata acctggctga cccgattccg cggacaccgc tgcagccgcg      60
gctggagcca gggcgccggt gccccgcgct ctccccggtc ttgcgctgcg ggggccatac     120
cgcctctgtg acttctttgc gggccaggga cggagaagga gtctgtgcct gagaaactgg     180
gctctgtgcc caggcgcgag gtgcaggatg gagagcaagg cgctgctagc tgtcgctctg     240
tggttctgcg tggagacccg agccgcctct gtgggtttga ctggcgattt tctccatccc     300
cccaagctca gcacacagaa agacatactg acaattttgg caaatacaac ccttcagatt     360
acttgcaggg gacagcggga cctggactgg ctttggccca atgctcagcg tgattctgag     420
gaaagggtat tggtgactga atgcggcggt ggtgacagta tcttctgcaa acactcacc      480 attcccaggg tggttggaaa tgatactgga gcctacaagt gctcgtaccg ggacgtcgac     540
atagcctcca ctgtttatgt ctatgttcga gattacagat caccattcat cgcctctgtc     600
agtgaccagc atggcatcgt gtacatcacc gagaacaaga caaaactgt ggtgatcccc     660 tgccgagggt cgatttcaaa cctcaatgtg tctctttgcg ctaggtatcc agaaaagaga     720
tttgttccgg atggaaacag aatttcctgg gacagcgaga taggctttac tctccccagt     780
tacatgatca gctatgccgg catggtcttc tgtgaggcaa agatcaatga tgaaacctat     840
cagtctatca tgtacatagt tgtggttgta ggatatagga tttatgatgt gattctgagc     900
cccccgcatg aaattgagct atctgccgga gaaaaacttg tcttaaattg tacagcgaga     960
acagagctca atgtggggct tgatttcacc tggcactctc caccttcaaa gtctcatcat    1020
aagaagatta taaccggga tgtgaaaccc tttcctggga ctgtggcgaa gatgttttg     1080 agcaccttga caatagaaag tgtgaccaag agtgaccaag gggaatacac ctgtgtagcg    1140
tccagtggac ggatgatcaa gagaaataga acatttgtcc gagttcacac aaagccttt     1200 attgctttcg gtagtgggat gaaatctttg gtggaagcca cagtgggcag tcaagtccga    1260
```

```
atccctgtga agtatctcag ttacccagct cctgatatca aatggtacag aaatggaagg    1320
cccattgagt ccaactacac aatgattgtt ggcgatgaac tcaccatcat ggaagtgact    1380
gaaagagatg caggaaacta cacggtcatc ctcaccaacc ccatttcaat ggagaaacag    1440
agccacatgg tctctctggt tgtgaatgtc ccaccccaga tcggtgagaa agccttgatc    1500
tcgcctatgg attcctacca gtatgggacc atgcagacat tgacatgcac agtctacgcc    1560
aaccctcccc tgcaccacat ccagtggtac tggcagctag aagaagcctg ctcctacaga    1620
cccggccaaa caagcccgta tgcttgtaaa gaatggagac acgtggagga tttccagggg    1680
ggaaacaaga tcgaagtcac caaaaaccaa tatgccctga ttgaaggaaa aaacaaaact    1740
gtaagtacgc tggtcatcca agctgccaac gtgtcagcgt tgtacaaatg tgaagccatc    1800
aacaaagcgg gacgaggaga gagggtcatc tccttccatg tgatcagggg tcctgaaatt    1860
actgtgcaac ctgctgccca gccaactgag caggagagtg tgtccctgtt gtgcactgca    1920
gacagaaata cgtttgagaa cctcacgtgg tacaagcttg gctcacaggc aacatcggtc    1980
cacatgggcg aatcactcac accagtttgc aagaacttgg atgctctttg gaaactgaat    2040
ggcaccatgt tttctaacag cacaaatgac atcttgattg tggcatttca gaatgcctct    2100
ctgcaggacc aaggcgacta tgtttgctct gctcaagata agaagaccaa gaaaagacat    2160
tgcctggtca acagctcat catcctagag cgcatggcac ccatgatcac cggaaatctg    2220
gagaatcaga caacaaccat tggcgagacc attgaagtga cttgcccagc atctggaaat    2280
cctaccccac acattacatg gttcaaagac aacgagaccc tggtagaaga ttcaggcatt    2340
gtactgagag atgggaaccg gaacctgact atccgcaggg tgaggaagga ggatggaggc    2400
ctctacacct gccaggcctg caatgtcctt ggctgtgcaa gagcggagac gctcttcata    2460
atagaaggtg cccaggaaaa gaccaacttg gaagtcatta tcctcgtcgg cactgcagtg    2520
attgccatgt tcttctggct ccttcttgtc attgtcctac ggaccgttaa gcgggccaat    2580
gaagggaac tgaagacagg ctacttgtct attgtcatgg atccagatga attgcccttg    2640
gatgagcgct gtgaacgctt gccttatgat gccagcaagt gggaattccc cagggaccgg    2700
ctgaaactag gaaaacctct tggccgcggt gccttcggcc aagtgattga ggcagacgct    2760
tttggaattg acaagacagc gacttgcaaa acagtagccg tcaagatgtt gaaagaagga    2820
gcaacacaca gcgagcatcg agccctcatg tctgaactca gatcctcat ccacattggt    2880
caccatctca atgtggtgaa cctcctaggc gcctgcacca gccgggagg gcctctcatg    2940
gtgattgtga aattctgcaa gtttggaaac ctatcaactt acttacgggg caagagaaat    3000
gaatttgttc cctataagag caaaggggca cgcttccgcc agggcaagga ctacgttggg    3060
gagctctccg tggatctgaa aagacgcttg gacagcatca ccagcagcca gagctctgcc    3120
agctcaggct tgttgaagga gaaatcgctc agtgatgtag aggaagaaga agcttctgaa    3180
gaactgtaca aggacttcct gaccttggag catctcatct gttacagctt ccaagtggct    3240
aagggcatgg agttcttggc atcaaggaag tgtatccaca gggacctggc agcacgaaac    3300
attctcctat cggagaagaa tgtggttaag atctgtgact cggcttggc ccgggacatt    3360
tataaagacc cggattatgt cagaaaagga gatgcccgac tccctttgaa gtggatggcc    3420
ccggaaacca ttttgacag agtatacaca attcagagcg atgtgtggtc tttcggtgtg    3480
ttgctctggg aaatattttc cttaggtgcc tccccatacc ctgggggtca agattgatgaa    3540
gaattttgta ggagattgaa agaaggaact agaatgcggg ctcctgacta cactacccca    3600
gaaatgtacc agaccatgct ggactgctgg catgaggacc ccaaccagag accctcgttt    3660
```

-continued

```
tcagagttgg tggagcattt gggaaacctc ctgcaagcaa atgcgcagca ggatggcaaa    3720
gactatattg ttcttccaat gtcagagaca ctgagcatgg aagaggattc tggactctcc    3780
ctgcctacct cacctgtttc ctgtatggag gaagaggaag tgtgcgaccc caaattccat    3840
tatgacaaca cagcaggaat cagtcattat ctccagaaca gtaagcgaaa gagccggcca    3900
gtgagtgtaa aaacatttga agatatccca ttggaggaac cagaagtaaa agtgatccca    3960
gatgacagcc agacagacag tgggatggtc cttgcatcag aagagctgaa aactctggaa    4020
gacaggaaca aattatctcc atcttttggt ggaatgatgc ccagtaaaag cagggagtct    4080
gtggcctcgg aaggctccaa ccagaccagt ggctaccagt ctgggtatca ctcagatgac    4140
acagacacca ccgtgtactc cagcgacgag gcaggacttt taaagatggt ggatgctgca    4200
gttcacgctg actcagggac cacactcgcc tcacctcctg tttaaatgga agtggtcctg    4260
tcccggctcc gcccccaact cctggaaatc acgagagagg tgctgcttag attttcaagt    4320
gttgttcttt ccaccacccg gaagtagcca catttgattt tcattttttgg aggagggacc    4380 tcagactgca aggagcttgt cctcagggca tttccagaga agatgcccat gacccaagaa    4440
tgtgttgact ctactctctt ttccattcat ttaaaagtcc tatataatgt gccctgctgt    4500
ggtctcacta ccagttaaag caaaagactt tcaaacacgt ggactctgtc ctccaagaag    4560
tggcaacggc acctctgtga aactggatcg aatgggcaat gctttgtgtg ttgaggatgg    4620
gtgagatgtc ccagggccga gtctgtctac cttggaggct ttgtggagga tgcggctatg    4680
agccaagtgt taagtgtggg atgtggactg gaggaagga aggcgcaagt cgctcggaga    4740
gcggttggag cctgcagatg cattgtgctg gctctggtgg aggtgggctt gtggcctgtc    4800
aggaaacgca aaggcggccg gcagggtttg gttttggaag gtttgcgtgc tcttcacagt    4860
cgggttacag gcgagttccc tgtggcgttt cctactccta atgagagttc cttccggact    4920
cttacgtgtc tcctggcctg gccccaggaa ggaaatgatg cagcttgctc cttcctcatc    4980
tctcaggctg tgccttaatt cagaacacca aaagagagga acgtcggcag aggctcctga    5040
cggggccgaa gaattgtgag aacagaacag aaactcaggg tttctgctgg gtggagaccc    5100
acgtggcgcc ctggtggcag gtctgagggt ctctgtcaa gtggcggtaa aggctcaggc    5160
tggtgttctt cctctatctc cactcctgtc aggcccccaa gtcctcagta ttttagcttt    5220
gtggcttcct gatggcagaa aaatcttaat tggttggttt gctctccaga taatcactag    5280
ccagatttcg aaattacttt ttagccgagg ttatgataac atctactgta tcctttagaa    5340
ttttaaccta taaaactatg tctactggtt tctgcctgtg tgcttatgtt               5390
```

<210> SEQ ID NO 6
<211> LENGTH: 1345
<212> TYPE: PRT
<213> ORGANISM: mouse

<400> SEQUENCE: 6

```
Met Glu Ser Lys Ala Leu Leu Ala Val Ala Leu Trp Phe Cys Val Glu
1               5                   10                  15

Thr Arg Ala Ala Ser Val Gly Leu Thr Gly Asp Phe Leu His Pro Pro
            20                  25                  30

Lys Leu Ser Thr Gln Lys Asp Ile Leu Thr Ile Leu Ala Asn Thr Thr
        35                  40                  45

Leu Gln Ile Thr Cys Arg Gly Gln Arg Asp Leu Asp Trp Leu Trp Pro
    50                  55                  60

Asn Ala Gln Arg Asp Ser Glu Glu Arg Val Leu Val Thr Glu Cys Gly
65                  70                  75                  80
```

```
Gly Gly Asp Ser Ile Phe Cys Lys Thr Leu Thr Ile Pro Arg Val Val
                85                  90                  95
Gly Asn Asp Thr Gly Ala Tyr Lys Cys Ser Tyr Arg Asp Val Asp Ile
                100                 105                 110
Ala Ser Thr Val Tyr Val Tyr Val Arg Asp Tyr Arg Ser Pro Phe Ile
                115                 120                 125
Ala Ser Val Ser Asp Gln His Gly Ile Val Tyr Ile Thr Glu Asn Lys
                130                 135                 140
Asn Lys Thr Val Val Ile Pro Cys Arg Gly Ser Ile Ser Asn Leu Asn
145                 150                 155                 160
Val Ser Leu Cys Ala Arg Tyr Pro Glu Lys Arg Phe Val Pro Asp Gly
                165                 170                 175
Asn Arg Ile Ser Trp Asp Ser Glu Ile Gly Phe Thr Leu Pro Ser Tyr
                180                 185                 190
Met Ile Ser Tyr Ala Gly Met Val Phe Cys Glu Ala Lys Ile Asn Asp
                195                 200                 205
Glu Thr Tyr Gln Ser Ile Met Tyr Ile Val Val Val Gly Tyr Arg
                210                 215                 220
Ile Tyr Asp Val Ile Leu Ser Pro Pro His Glu Ile Glu Leu Ser Ala
225                 230                 235                 240
Gly Glu Lys Leu Val Leu Asn Cys Thr Ala Arg Thr Glu Leu Asn Val
                245                 250                 255
Gly Leu Asp Phe Thr Trp His Ser Pro Pro Ser Lys Ser His His Lys
                260                 265                 270
Lys Ile Val Asn Arg Asp Val Lys Pro Phe Pro Gly Thr Val Ala Lys
                275                 280                 285
Met Phe Leu Ser Thr Leu Thr Ile Glu Ser Val Thr Lys Ser Asp Gln
                290                 295                 300
Gly Glu Tyr Thr Cys Val Ala Ser Ser Gly Arg Met Ile Lys Arg Asn
305                 310                 315                 320
Arg Thr Phe Val Arg Val His Thr Lys Pro Phe Ile Ala Phe Gly Ser
                325                 330                 335
Gly Met Lys Ser Leu Val Glu Ala Thr Val Gly Ser Gln Val Arg Ile
                340                 345                 350
Pro Val Lys Tyr Leu Ser Tyr Pro Ala Pro Asp Ile Lys Trp Tyr Arg
                355                 360                 365
Asn Gly Arg Pro Ile Glu Ser Asn Tyr Thr Met Ile Val Gly Asp Glu
                370                 375                 380
Leu Thr Ile Met Glu Val Thr Glu Arg Asp Ala Gly Asn Tyr Thr Val
385                 390                 395                 400
Ile Leu Thr Asn Pro Ile Ser Met Glu Lys Gln Ser His Met Val Ser
                405                 410                 415
Leu Val Val Asn Val Pro Pro Gln Ile Gly Glu Lys Ala Leu Ile Ser
                420                 425                 430
Pro Met Asp Ser Tyr Gln Tyr Gly Thr Met Gln Thr Leu Thr Cys Thr
                435                 440                 445
Val Tyr Ala Asn Pro Pro Leu His His Ile Gln Trp Tyr Trp Gln Leu
                450                 455                 460
Glu Glu Ala Cys Ser Tyr Arg Pro Gly Gln Thr Ser Pro Tyr Ala Cys
465                 470                 475                 480
Lys Glu Trp Arg His Val Glu Asp Phe Gln Gly Gly Asn Lys Ile Glu
                485                 490                 495
Val Thr Lys Asn Gln Tyr Ala Leu Ile Glu Gly Lys Asn Lys Thr Val
```

-continued

```
                500                 505                 510
Ser Thr Leu Val Ile Gln Ala Ala Asn Val Ser Ala Leu Tyr Lys Cys
            515                 520                 525

Glu Ala Ile Asn Lys Ala Gly Arg Gly Glu Arg Val Ile Ser Phe His
            530                 535                 540

Val Ile Arg Gly Pro Glu Ile Thr Val Gln Pro Ala Ala Gln Pro Thr
545                 550                 555                 560

Glu Gln Glu Ser Val Ser Leu Leu Cys Thr Ala Asp Arg Asn Thr Phe
                565                 570                 575

Glu Asn Leu Thr Trp Tyr Lys Leu Gly Ser Gln Ala Thr Ser Val His
            580                 585                 590

Met Gly Glu Ser Leu Thr Pro Val Cys Lys Asn Leu Asp Ala Leu Trp
            595                 600                 605

Lys Leu Asn Gly Thr Met Phe Ser Asn Ser Thr Asn Asp Ile Leu Ile
            610                 615                 620

Val Ala Phe Gln Asn Ala Ser Leu Gln Asp Gln Gly Asp Tyr Val Cys
625                 630                 635                 640

Ser Ala Gln Asp Lys Lys Thr Lys Lys Arg His Cys Leu Val Lys Gln
                645                 650                 655

Leu Ile Ile Leu Glu Arg Met Ala Pro Met Ile Thr Gly Asn Leu Glu
            660                 665                 670

Asn Gln Thr Thr Thr Ile Gly Glu Thr Ile Glu Val Thr Cys Pro Ala
            675                 680                 685

Ser Gly Asn Pro Thr Pro His Ile Thr Trp Phe Lys Asp Asn Glu Thr
            690                 695                 700

Leu Val Glu Asp Ser Gly Ile Val Leu Arg Asp Gly Asn Arg Asn Leu
705                 710                 715                 720

Thr Ile Arg Arg Val Arg Lys Glu Asp Gly Gly Leu Tyr Thr Cys Gln
                725                 730                 735

Ala Cys Asn Val Leu Gly Cys Ala Arg Ala Glu Thr Leu Phe Ile Ile
            740                 745                 750

Glu Gly Ala Gln Glu Lys Thr Asn Leu Glu Val Ile Ile Leu Val Gly
            755                 760                 765

Thr Ala Val Ile Ala Met Phe Phe Trp Leu Leu Leu Val Ile Val Leu
            770                 775                 780

Arg Thr Val Lys Arg Ala Asn Glu Gly Glu Leu Lys Thr Gly Tyr Leu
785                 790                 795                 800

Ser Ile Val Met Asp Pro Asp Glu Leu Pro Leu Asp Glu Arg Cys Glu
                805                 810                 815

Arg Leu Pro Tyr Asp Ala Ser Lys Trp Glu Phe Pro Arg Asp Arg Leu
            820                 825                 830

Lys Leu Gly Lys Pro Leu Gly Arg Gly Ala Phe Gly Gln Val Ile Glu
            835                 840                 845

Ala Asp Ala Phe Gly Ile Asp Lys Thr Ala Thr Cys Lys Thr Val Ala
            850                 855                 860

Val Lys Met Leu Lys Glu Gly Ala Thr His Ser Glu His Arg Ala Leu
865                 870                 875                 880

Met Ser Glu Leu Lys Ile Leu Ile His Ile Gly His His Leu Asn Val
                885                 890                 895

Val Asn Leu Leu Gly Ala Cys Thr Lys Pro Gly Gly Pro Leu Met Val
            900                 905                 910

Ile Val Glu Phe Cys Lys Phe Gly Asn Leu Ser Thr Tyr Leu Arg Gly
            915                 920                 925
```

-continued

```
Lys Arg Asn Glu Phe Val Pro Tyr Lys Ser Lys Gly Ala Arg Phe Arg
            930                 935                 940
Gln Gly Lys Asp Tyr Val Gly Glu Leu Ser Val Asp Leu Lys Arg Arg
945                 950                 955                 960
Leu Asp Ser Ile Thr Ser Ser Gln Ser Ser Ala Ser Ser Gly Phe Val
                965                 970                 975
Glu Glu Lys Ser Leu Ser Asp Val Glu Glu Glu Ala Ser Glu Glu
            980                 985                 990
Leu Tyr Lys Asp Phe Leu Thr Leu Glu His Leu Ile Cys Tyr Ser Phe
            995                 1000                1005
Gln Val Ala Lys Gly Met Glu Phe Leu Ala Ser Arg Lys Cys Ile His
        1010                1015                1020
Arg Asp Leu Ala Ala Arg Asn Ile Leu Leu Ser Glu Lys Asn Val Val
1025                1030                1035                1040
Lys Ile Cys Asp Phe Gly Leu Ala Arg Asp Ile Tyr Lys Asp Pro Asp
                1045                1050                1055
Tyr Val Arg Lys Gly Asp Ala Arg Leu Pro Leu Lys Trp Met Ala Pro
                1060                1065                1070
Glu Thr Ile Phe Asp Arg Val Tyr Thr Ile Gln Ser Asp Val Trp Ser
        1075                1080                1085
Phe Gly Val Leu Leu Trp Glu Ile Phe Ser Leu Gly Ala Ser Pro Tyr
        1090                1095                1100
Pro Gly Val Lys Ile Asp Glu Glu Phe Cys Arg Arg Leu Lys Glu Gly
1105                1110                1115                1120
Thr Arg Met Arg Ala Pro Asp Tyr Thr Thr Pro Glu Met Tyr Gln Thr
                1125                1130                1135
Met Leu Asp Cys Trp His Glu Asp Pro Asn Gln Arg Pro Ser Phe Ser
                1140                1145                1150
Glu Leu Val Glu His Leu Gly Asn Leu Leu Gln Ala Asn Ala Gln Gln
        1155                1160                1165
Asp Gly Lys Asp Tyr Ile Val Leu Pro Met Ser Glu Thr Leu Ser Met
        1170                1175                1180
Glu Glu Asp Ser Gly Leu Ser Leu Pro Thr Ser Pro Val Ser Cys Met
1185                1190                1195                1200
Glu Glu Glu Glu Val Cys Asp Pro Lys Phe His Tyr Asp Asn Thr Ala
                1205                1210                1215
Gly Ile Ser His Tyr Leu Gln Asn Ser Lys Arg Lys Ser Arg Pro Val
                1220                1225                1230
Ser Val Lys Thr Phe Glu Asp Ile Pro Leu Glu Glu Pro Glu Val Lys
        1235                1240                1245
Val Ile Pro Asp Asp Ser Gln Thr Asp Ser Gly Met Val Leu Ala Ser
        1250                1255                1260
Glu Glu Leu Lys Thr Leu Glu Asp Arg Asn Lys Leu Ser Pro Ser Phe
1265                1270                1275                1280
Gly Gly Met Met Pro Ser Lys Ser Arg Glu Ser Val Ala Ser Glu Gly
                1285                1290                1295
Ser Asn Gln Thr Ser Gly Tyr Gln Ser Gly Tyr His Ser Asp Asp Thr
                1300                1305                1310
Asp Thr Thr Val Tyr Ser Ser Asp Glu Ala Gly Leu Leu Lys Met Val
        1315                1320                1325
Asp Ala Ala Val His Ala Asp Ser Gly Thr Thr Leu Arg Ser Pro Pro
        1330                1335                1340
Val
1345
```

```
<210> SEQ ID NO 7
<211> LENGTH: 9
<212> TYPE: PRT
<213> ORGANISM: Mus musculus

<400> SEQUENCE: 7

Arg Gly Gln Arg Asp Leu Asp Trp Leu
1               5

<210> SEQ ID NO 8
<211> LENGTH: 9
<212> TYPE: PRT
<213> ORGANISM: Mus musculus

<400> SEQUENCE: 8

Thr Tyr Gln Ser Ile Met Tyr Ile Val
1               5

<210> SEQ ID NO 9
<211> LENGTH: 9
<212> TYPE: PRT
<213> ORGANISM: Mus musculus

<400> SEQUENCE: 9

Val Gly Tyr Arg Ile Tyr Asp Val Ile
1               5

<210> SEQ ID NO 10
<211> LENGTH: 9
<212> TYPE: PRT
<213> ORGANISM: Mus musculus

<400> SEQUENCE: 10

Trp Tyr Arg Asn Gly Arg Pro Ile Glu
1               5

<210> SEQ ID NO 11
<211> LENGTH: 9
<212> TYPE: PRT
<213> ORGANISM: Mus musculus

<400> SEQUENCE: 11

Gln Tyr Gly Thr Met Gln Thr Leu Thr
1               5

<210> SEQ ID NO 12
<211> LENGTH: 9
<212> TYPE: PRT
<213> ORGANISM: Mus musculus

<400> SEQUENCE: 12

Leu Gly Cys Ala Arg Ala Glu Thr Leu
1               5

<210> SEQ ID NO 13
<211> LENGTH: 9
<212> TYPE: PRT
<213> ORGANISM: Mus musculus

<400> SEQUENCE: 13

Glu Gly Glu Leu Lys Thr Gly Tyr Leu
1               5

<210> SEQ ID NO 14
```

```
<211> LENGTH: 9
<212> TYPE: PRT
<213> ORGANISM: Mus musculus

<400> SEQUENCE: 14

Leu Tyr Lys Asp Phe Leu Tyr Thr Glu
 1               5

<210> SEQ ID NO 15
<211> LENGTH: 9
<212> TYPE: PRT
<213> ORGANISM: Mus musculus

<400> SEQUENCE: 15

Gln Arg Pro Ser Phe Ser Glu Leu Val
 1               5

<210> SEQ ID NO 16
<211> LENGTH: 9
<212> TYPE: PRT
<213> ORGANISM: Mus musculus

<400> SEQUENCE: 16

Glu Leu Val Glu His Leu Gly Asn Leu
 1               5

<210> SEQ ID NO 17
<211> LENGTH: 9
<212> TYPE: PRT
<213> ORGANISM: Artificial Sequence
<220> FEATURE:
<223> OTHER INFORMATION: HIVtat

<400> SEQUENCE: 17

Arg Lys Lys Arg Arg Gln Arg Arg Arg
 1               5

<210> SEQ ID NO 18
<211> LENGTH: 9
<212> TYPE: PRT
<213> ORGANISM: Mus musculus

<400> SEQUENCE: 18

Arg Val Val Gly Asn Asp Thr Gly Ala
 1               5

<210> SEQ ID NO 19
<211> LENGTH: 9
<212> TYPE: PRT
<213> ORGANISM: Mus musculus

<400> SEQUENCE: 19

Val Ile Leu Thr Asn Pro Ile Ser Met
 1               5

<210> SEQ ID NO 20
<211> LENGTH: 9
<212> TYPE: PRT
<213> ORGANISM: Mus musculus

<400> SEQUENCE: 20

Phe His Tyr Asp Asn Thr Ala Gly Ile
 1               5

<210> SEQ ID NO 21
<211> LENGTH: 9
```

```
-continued

<212> TYPE: PRT
<213> ORGANISM: Mus musculus

<400> SEQUENCE: 21

Arg Gly Gln Arg Asp Leu Asp Trp Leu
 1               5

<210> SEQ ID NO 22
<211> LENGTH: 9
<212> TYPE: PRT
<213> ORGANISM: Mus musculus

<400> SEQUENCE: 22

Val Ile Ala Met Phe Phe Trp Leu Leu
 1               5

<210> SEQ ID NO 23
<211> LENGTH: 10
<212> TYPE: PRT
<213> ORGANISM: Mus musculus

<400> SEQUENCE: 23

Thr Thr Pro Glu Met His Tyr Gln Thr Met
 1               5                  10
```